(12) United States Patent
Kim et al.

(10) Patent No.: US 12,128,041 B2
(45) Date of Patent: Oct. 29, 2024

(54) NANOPARTICLES FOR DELIVERING DRUG, WHOSE SURFACE IS MODIFIED WITH PEPTIDE FOR TARGETING BRAIN CANCER, PREPARATION METHOD THEREOF AND USE THEREOF

(71) Applicant: UNIVERSITY-INDUSTRY COOPERATION GROUP OF KYUNG HEE UNIVERSITY, Gyeonggi-do (KR)

(72) Inventors: Dokyoung Kim, Seoul (KR); Hyo Young Kim, Seoul (KR); Rae Hyung Kang, Gyeonggi-do (KR)

(73) Assignee: UNIVERSITY-INDUSTRY COOPERATION GROUP OF KYUNG HEE UNIVERSITY, Gyeonggi-do (KR)

(*) Notice: Subject to any disclaimer, the term of this patent is extended or adjusted under 35 U.S.C. 154(b) by 670 days.

(21) Appl. No.: 17/311,902

(22) PCT Filed: Dec. 30, 2020

(86) PCT No.: PCT/KR2020/019402
§ 371 (c)(1),
(2) Date: Jun. 8, 2021

(87) PCT Pub. No.: WO2021/141319
PCT Pub. Date: Jul. 15, 2021

(65) Prior Publication Data
US 2022/0323432 A1     Oct. 13, 2022

(30) Foreign Application Priority Data
Jan. 8, 2020  (KR) .................. 10-2020-0002725

(51) Int. Cl.
*A61K 31/4745* (2006.01)
*A61K 9/51* (2006.01)
(Continued)

(52) U.S. Cl.
CPC ........ *A61K 31/4745* (2013.01); *A61K 9/5115* (2013.01); *A61K 47/595* (2017.08);
(Continued)

(58) Field of Classification Search
CPC ............... A61K 31/4745; A61K 47/64; A61K 47/6925; A61K 47/595; A61K 9/5115; A61P 35/00
See application file for complete search history.

(56) References Cited

U.S. PATENT DOCUMENTS 10,717,735 B2 *  7/2020  Ibrahim ............... C07D 471/04

FOREIGN PATENT DOCUMENTS

| KR | 10-1095841 B1 | 12/2011 | |
| KR | 10-1647804 B1 | 8/2016 | |
| KR | 10-2019-0078409 A | 7/2019 | |
| WO | WO-2018146166 A1 * | 8/2018 | ............. A61K 47/64 |

OTHER PUBLICATIONS

English Translation of FKR1020190078409A, Pub. Date: Aug. 2018 (Year: 2018).*
(Continued)

*Primary Examiner* — Carlos A Azpuru
(74) *Attorney, Agent, or Firm* — Harness, Dickey & Pierce, P.L.C.

(57) ABSTRACT

The present disclosure relates to nanoparticles for delivering a drug targeting brain cancer, whose surface is modified with a peptide for targeting brain cancer, a preparation method thereof, and a use thereof, and more particularly, to nanoparticles for delivering a drug targeting brain cancer, including porous silicon nanoparticles encapsulating an anti-
(Continued)

cancer drug and a peptide with an ability to target brain cancer cells bound to the surface of the nanoparticles, a preparation method thereof, and a use thereof. The nanoparticles according to the present disclosure can be used as an effective drug delivery system for treating glioblastoma by allowing a conventional anticancer agent exhibiting low tissue specificity and solubility to be specifically delivered to glioblastoma in which a caveolin receptor is overexpressed through the blood-brain barrier to induce a more efficient glioblastoma therapeutic effect.

13 Claims, 24 Drawing Sheets

Specification includes a Sequence Listing.

(51) Int. Cl.
*A61K 47/59* (2017.01)
*A61K 47/64* (2017.01)
*A61K 47/69* (2017.01)
*A61P 35/00* (2006.01)

(52) U.S. Cl.
CPC .......... *A61K 47/64* (2017.08); *A61K 47/6925* (2017.08); *A61P 35/00* (2018.01)

(56) References Cited

OTHER PUBLICATIONS

McCord et al., Folate Receptors' Expression in Gliomas May Possess Potential Nanoparticle-Based Drug Delivery Opportunities. ACS Omega. Feb. 1, 2021;6(6):4111-4118. doi: 10.1021/acsomega. 0c05500. PMID: 33623837; PMCID: PMC7893640 (Year: 2021).*
Patlolla et al. (2008) Folate-targeted etoposide-encapsulated lipid nanospheres, Journal of Drug Targeting, 16:4, 269-275, DOI: 10.1080/10611860801945400. (Year: 2008).*
Kang , A Brain Tumor-Homing Tetra-Peptide Delivers a Nano-Therapeutic for More Effective Treatment of a Mouse Model of Glioblastoma, Nanoscale Horizons, pp. 2013-2025. (Year: 2020).*
Nat Mater. Apr. 2008; 8(4): 331-336.

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: glioblastoma targeting peptide

<400> SEQUENCE: 1

Ser Ile Trp Val
1

NANOPARTICLES FOR DELIVERING DRUG, WHOSE SURFACE IS MODIFIED WITH PEPTIDE FOR TARGETING BRAIN CANCER, PREPARATION METHOD THEREOF AND USE THEREOF

CROSS-REFERENCE TO RELATED APPLICATIONS

This application is a national phase application of PCT Application No. PCT/KR2020/019402, filed on Dec. 30, 2020, which claims the benefit of and priority to Korean Patent Application No. 10-2020-0002725, filed on Jan. 8, 2020. The entire disclosures of the applications identified in this paragraph are incorporated herein by references.

TECHNICAL FIELD

The present disclosure relates to nanoparticles for delivering a drug targeting brain cancer, whose surface is modified with a peptide for targeting brain cancer, a preparation method thereof, and a use thereof, and more particularly, to nanoparticles for delivering a drug targeting brain cancer, including porous silicon nanoparticles encapsulating an anticancer drug and a peptide with an ability to target brain cancer cells bound to the surface of the nanoparticles, a preparation method thereof, and a use thereof.

BACKGROUND ART

Cell-penetrating peptides (CPPs) are short cell-penetrating peptides including about 10 to 30 amino acids, and after it was revealed that the cell-penetrating peptides have an ability to efficiently transport various materials such as small/large organic molecules, inorganic materials and nanoparticles into cells, various applied studies using the same have been conducted. Cell-penetrating peptides generally identified in viruses, artificial synthetic sequences, or phage display selections have been widely used as tools for basic research, and frequently used as a constituent component of many drug delivery systems under development. However, cell-penetrating peptides reported to date have general limitations such as (i) low tissue selectivity, (ii) non-specific cell permeation (iii) rapid removal in the kidney, the spleen, and the liver due to inherent cationic properties (for example, TAT, AntpR8). To overcome these limitations, researchers focused on hydrophobic and non-ionic cell-penetrating peptides having a high affinity for cell membrane receptors which are overexpressed in specific cells. For example, an anti-HER2/neu peptide can target HER2/neu-positive breast cancer cells, and DV3 can target CXC chemokine receptor 4 (CXCR4) which is overexpressed in various cancer cells. The specificity of targeting such specific cells can be further increased by linking non-CPP targeting amino acid sequences (for example, MMP) having a specificity that binds to the receptors of those target cells.

In general, cell-penetrating peptides flow into cells through permeation pathways using specific molecules such as heparan sulfate, clathrin, caveolin and phospholipids expressed in the cell membrane. The efficiency of cell-penetrating peptides depends on these factors, and the effects of hydrophobic cell-penetrating peptides are more pronounced. In this respect, the design strategy of new cell-penetrating peptides must be established by target cells and tissues.

Meanwhile, glioblastoma is the most representative carcinoma that occurs in the brain, and is a malignant tumor with an average survival period of 12 to 15 months after diagnosis and a 5-year survival rate of less than 5%. Although palliative therapies such as chemotherapy have been demonstrated as a method for treating glioblastoma, the low tissue selectivity and low blood-brain barrier penetration rate of a drug cause many side effects.

In such a context, a nanoparticle-based drug delivery system has attracted attention as a method for solving these problems. Among the nanomaterials known in the art, porous silicon nanoparticles have been widely applied to preclinical studies due to low toxicity, their inherent photoluminescence characteristics, a high loading efficiency, and an advantage capable of easily controlling a release system (Nat Mater. 2009 April; 8 (4): 331-6).

Thus, the present inventors manufactured a new porous silicon nanoparticle-based nano drug delivery system by loading an anticancer drug 7-ethyl-10-hydroxy-camptothecin into the porous silicon nanoparticles and binding a cell-penetrating peptide having an ability to target glioblastoma to the surface of the nanoparticles as a therapeutic strategy for glioblastoma.

SUMMARY

Technical Problem

As described above, the present inventors loaded an anticancer drug using a nanoparticle-based drug delivery system, developed nanoparticles for delivering a drug targeting glioblastoma cells, to which a peptide with an ability to target glioblastoma is attached, and confirmed an excellent targeting function and an excellent therapeutic effect thereof, thereby completing the present disclosure.

Thus, an object of the present disclosure is to provide nanoparticles for delivering a drug targeting brain cancer cells, including: (i) porous silicon nanoparticle encapsulating an anticancer drug and (ii) a peptide including an amino acid sequence of SEQ ID NO: 1, which binds to the surface of the nanoparticles.

Further, another object of the present disclosure is to provide a pharmaceutical composition for treating brain cancer, including the nanoparticles as an active ingredient.

In addition, still another object of the present disclosure is to provide a method of preparing the nanoparticles.

However, technical problems to be solved by the present disclosure are not limited to the aforementioned problems, and other problems that are not mentioned may be clearly understood by those skilled in the art from the following description.

Technical Solution

To achieve the objects of the present disclosure as described above, the present disclosure provides nanoparticles for delivering a drug targeting brain cancer, including: (i) porous silicon nanoparticle encapsulating an anticancer drug and (ii) a peptide including an amino acid sequence of SEQ ID NO: 1, which binds to the surface of the nanoparticles.

As an exemplary embodiment of the present disclosure, the brain cancer may be glioblastoma.

As another exemplary embodiment of the present disclosure, the drug may be 7-ethyl-10-hydroxy-camptothecin.

As still another exemplary embodiment of the present disclosure, the nanoparticles may be taken up by cells through a caveolin receptor.

As yet another exemplary embodiment of the present disclosure, the nanoparticles may pass through the blood-brain barrier (BBB).

As yet another exemplary embodiment of the present disclosure, the nanoparticle may have an average particle size of 100 to 500 nm.

As yet another exemplary embodiment of the present disclosure, the peptide may bind to the surface of the nanoparticles by a poly(ethylene glycol) linker.

Further, the present disclosure provides a pharmaceutical composition for treating brain cancer, including the nanoparticles as an active ingredient.

In addition, the present disclosure provides a method of preparing the nanoparticles, the method including: the following steps:
  (a) preparing porous silicon nanoparticles using a silicon wafer;
  (b) encapsulating an anticancer drug in the nanoparticles; and
  (c) binding a peptide including an amino acid sequence of SEQ ID NO: 1 targeting brain cancer cells to the surface of the nanoparticles encapsulating the anticancer drug by a linker.

As an exemplary embodiment of the present disclosure, in step (a), the nanoparticles may be prepared by preparing a porous silicon film using a silicon wafer, crushing the prepared porous silicon film in an ultrasonic bath, and then filtering the crushed porous silicon film using a syringe filter.

As another exemplary embodiment of the present disclosure, in step (a), the nanoparticles may have an average particle size of 100 to 200 nm.

As still another exemplary embodiment of the present disclosure, the linker may be poly(ethylene glycol).

In addition, the present disclosure provides a method of treating brain cancer, the method including: administering a pharmaceutical composition including the nanoparticles as an active ingredient to an individual.

Furthermore, the present disclosure provides a use of the pharmaceutical composition including the nanoparticles as an active ingredient for treating brain cancer.

Advantageous Effects

In the present disclosure, it was confirmed that porous silicon nanoparticles in which an anticancer drug is loaded and whose surface binds to a peptide targeting glioblastoma cells are absorbed into the glioblastoma cells and exhibit an excellent anticancer effect through specific drug delivery. Thus, the nanoparticles according to the present disclosure can be used as an effective drug delivery system for treating glioblastoma by allowing a conventional anticancer agent exhibiting low tissue specificity and solubility to be specifically delivered to glioblastoma in which a caveolin receptor is overexpressed through the blood-brain barrier to induce a more efficient glioblastoma therapeutic effect, so that the nanoparticles are expected to be useful in the clinical anticancer research field because the nanoparticles can improve the efficiency of an anticancer drug with poor in vivo distribution and can be applied to the treatment of cancer cells in which caveolin is overexpressed.

DETAILED DESCRIPTION

Figure 1A:
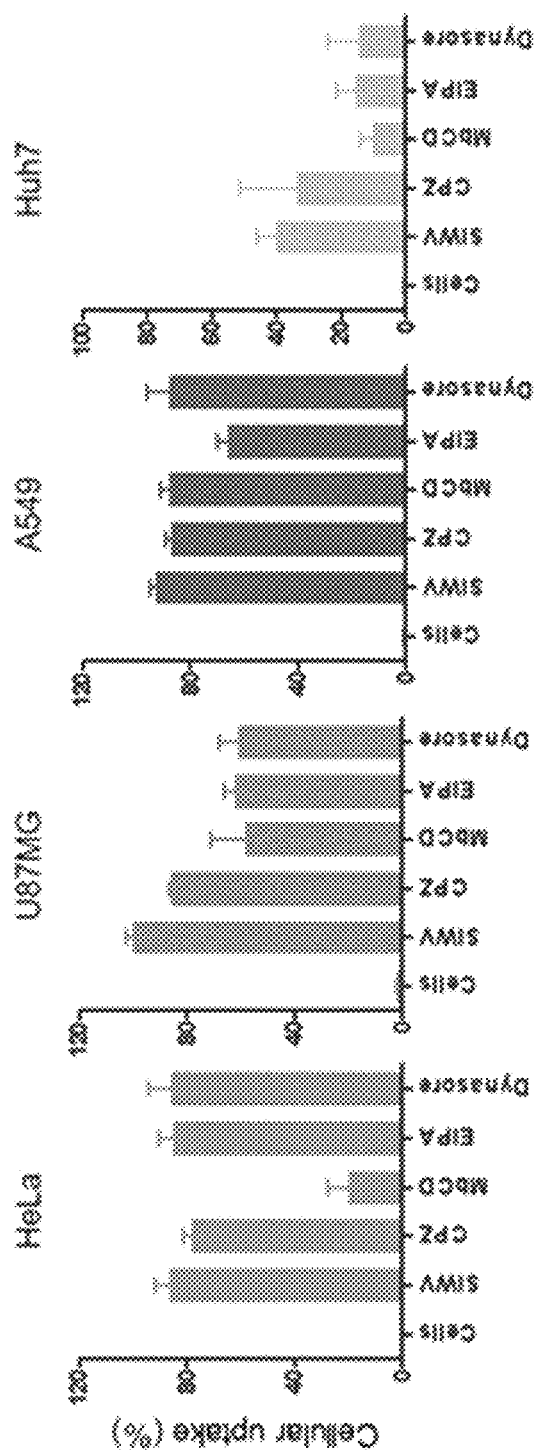
FIG. 1A shows the results of treating each of four types of cancer cell lines from different tissue origins with materials that specifically inhibit a known intracellular uptake pathway, and then treating the cancer cell lines with a SIWV peptide and measuring the intracellular uptake rate.

The present inventors loaded an anticancer drug using a nanoparticle-based drug delivery system, developed nanoparticles for delivering a drug targeting glioblastoma cells, to which a peptide with an ability to target glioblastoma is bound, and confirmed an excellent targeting function and an excellent therapeutic effect thereof, thereby completing the present disclosure.

Thus, the present disclosure provides nanoparticles for delivering a drug targeting brain cancer cells, including: (i) porous silicon nanoparticle encapsulating an anticancer drug and (ii) a peptide including an amino acid sequence of SEQ ID NO: 1, which binds to the surface of the nanoparticles.

As used herein, brain cancer, which is a target disease, refers to all cancers that occur in the cranium, is divided into primary and metastatic according to the site of origin, and the primary is again classified into gliomas, which invade the surrounding nerve tissue and non-gliomatous tumors, which compress the brain tissue without infiltrating the brain tissue. Depending on the degree of malignancy, brain cancer is classified into malignant brain tumors (malignant gliomas, cerebral metastatic cancer) and benign brain tumors (cerebral meningoma, vestibular schwannoma, pituitary tumors, benign gliomas), and malignant gliomas are divided into astrocytomas, oligodendrogliomas, ependymomas, and the like depending on the cells that constitute tumors. As used herein, brain cancer preferably refers to glioblastoma, but is not specifically limited as long as the brain cancer is a type of brain cancer to which a drug can be delivered by nanoparticles whose surface binds to a peptide according to the present disclosure.

The glioblastoma is most malignant in astrocytoma at grade 4, and histologically refers to an anaplastic astrocytoma with necrotic findings added. Glioblastoma is the most common primary brain tumor, accounts for 50% of gliomas and 15% of pediatric gliomas, and also includes giant cell glioblastoma, gliosarcoma, and the like according to the WHO classification table revised in 2000. Glioblastoma is treated by surgery to remove the tumor to the maximum extent and a combination of radiation therapy and chemotherapy, but the prognosis is very poor compared to other tumors, and treatment of glioblastoma usually slows tumor growth, and since it is difficult to inject drugs into the tumors, various studies have been conducted to overcome this limitation.

In the present disclosure, the anticancer drug is a drug for treating brain cancer, preferably glioblastoma, and more preferably, may be 7-ethyl-10-hydroxy-camptothecin, but other drugs for treating glioblastoma or brain cancer which the nanoparticles can target may be encapsulated.

The present inventors prepared the nanoparticles for delivering a drug targeting brain cancer cells as described above through Examples, confirmed the characteristics of the peptides and porous silicon nanoparticles constituting the nanoparticles, and confirmed the chemical characteristics and brain cancer therapeutic effects of the prepared nanoparticles.

More specifically, in an example of the present disclosure, various characteristics of a peptide having the amino acid sequence of SEQ ID NO: 1 bound to the surface of the nanoparticles according to the present disclosure were analyzed. As a result, it was confirmed that the peptide was taken up by cells by a caveolin receptor and specifically taken up by U87MG cells in which caveolin was overexpressed among various cell lines (see Example 1), and as a result of observing the pattern of in vivo distribution using mice, it was confirmed that the peptide was excreted from the body after about 24 hours and was specifically absorbed by the brain among various organs (see Example 2). Further, it was confirmed that by injecting the peptide into mice and removing the brain to perform a tissue analysis, the peptide did not stay only on the surface of the brain but passed through the blood-brain barrier and was taken up by the brain, (see Example 3), and as a result of injecting the peptide into a glioblastoma mouse model and analyzing whether the injected peptide targeted each organ, it could be seen that the peptide had an ability to target glioblastoma, through the fact that the peptide distribution in a brain site with glioblastoma was 2-fold higher than that of a control (see Example 4).

In another example of the present disclosure, porous silicon particles which are the basis of the nanoparticles according to the present disclosure were prepared (see Example 5), 7-ethyl-10-hydroxy-camptothecin (hereinafter, referred to as SN-38), which is a drug for treating glioblastoma porous silicon nanoparticles was loaded into the prepared silicon nanoparticles to prepare porous silicon nanoparticles loaded with the SN-38 drug, and as a result of analyzing the loading efficiency of the drug, it was confirmed that the loading efficiency was 28.7±4.5% (see Example 6).

In still another example of the present disclosure, nanoparticles for delivering a drug targeting brain cancer according to the present disclosure were prepared by binding a cell-penetrating peptide targeting glioblastoma to the surface of the porous silicon nanoparticles loaded with the drug. Thereafter, in order to analyze the characteristics of the prepared nanoparticles, the hydrodynamic size and zeta potential of the particles were measured, and it was confirmed that by analyzing the functional groups on the surface of the nanoparticles by observation with transmission electron microscopy and Fourier transform infrared spectroscopy (FT-IR), the peptide was attached to the surface of the nanoparticles (see Example 8).

The nanoparticles according to the present disclosure may have an average particle size of 100 to 500 nm, preferably 200 to 400 nm, more preferably 250 to 350 nm, and most preferably 306.2±32.7 nm.

In yet another example of the present disclosure, as a result of analyzing the drug release behavior of the nanoparticles according to the present disclosure, it was confirmed that most of the SN-38 drug was released within 2 hours and the rest was slowly released for 24 hours (see Example 9), and as a result of verifying the intracellular uptake and cytotoxicity of the nanoparticles, it was confirmed that the uptake into U87MG which is a glioblastoma cell line was effectively performed by attaching the peptide, and the concentration range showing an effective therapeutic effect on glioblastoma cells was investigated by confirming the degree of cytotoxicity depending on the treatment concentration of nanoparticles (see Example 10).

In yet another example of the present disclosure, as a result of investigating the in vivo distribution of the nanoparticles according to the present disclosure using a glioblastoma mouse model, it was confirmed that the nanoparticles were specifically distributed in the brain due to the ability to target glioblastoma (see Example 11), and as a result of injecting the nanoparticles into the glioblastoma mouse model according to an experimental protocol and analyzing the results in order to verify the substantive therapeutic effect on glioblastoma, the result that the size and volume of glioblastoma tumors were remarkably reduced was confirmed (see Example 12).

The results of the examples demonstrate that the nanoparticles according to the present disclosure have an excellent ability to target brain cancer, thereby inducing an excellent therapeutic effect.

Thus, as another aspect of the present disclosure, the present disclosure provides a pharmaceutical composition for treating brain cancer including, as an active ingredient, nanoparticles for delivering a drug targeting brain cancer cells, including: (i) porous silicon nanoparticle encapsulating an anticancer drug and (ii) a peptide including an amino acid sequence of SEQ ID NO: 1, which binds to the surface of the nanoparticles.

In the present disclosure, the brain cancer may be preferably glioblastoma, but is not limited thereto.

As used herein, the term "treatment" refers to all actions that ameliorate or beneficially change symptoms caused by brain cancer by administering the pharmaceutical composition according to the present disclosure.

The pharmaceutical composition according to the present disclosure includes the nanoparticles for delivering a drug targeting brain cancer cells as an active ingredient, and may further include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the oral composition according to the present disclosure may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in Remington's literature. The pharmaceutical composition of the present disclosure is not particularly limited in formulation, but may be formulated into an injection, an inhalant, an external preparation for skin, or the like.

The pharmaceutical composition of the present disclosure may be orally administered or may be parenterally administered (for example, applied intravenously, subcutaneously, intraperitoneally, or locally), and the administration dose may vary depending on a patient's condition and body weight, severity of disease, drug form, and administration route and period according to the target method, but the administration dose may be properly selected by those skilled in the art.

The pharmaceutical composition of the present disclosure is administered in a pharmaceutically effective amount. As used herein, the "pharmaceutically effective amount" refers to an amount sufficient for treating or diagnosing diseases at a reasonable benefit/risk ratio applicable to medical treatment or diagnosis, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field. The pharmaceutical composition according to the present disclosure may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present disclosure may vary depending on the age, sex, condition, and body weight of a patient, the absorption of the active ingredients in the body, inert rate and excretion rate, disease type, and the drugs used in combination, and in general, 0.001 to 150 mg, preferably 0.001 to 100 mg of the pharmaceutical composition of the present disclosure per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present disclosure in any way.

As still another aspect of the present disclosure, the present disclosure provides a method of treating brain cancer, the method including: administering a pharmaceutical composition including the nanoparticles as an active ingredient to an individual.

As used herein, the "individual" refers to a subject in need of treatment of a disease, and more specifically, refers to a mammal such as a human or a non-human primate, a mouse, a rat, a dog, a cat, a horse, and a cow.

As yet another aspect of the present disclosure, the present disclosure provides a use of the pharmaceutical composition for treating brain cancer.

As yet another aspect of the present disclosure, the present disclosure provides a method of preparing the nanoparticles, the method including the following steps:

(a) preparing porous silicon nanoparticles using a silicon wafer;

(b) encapsulating an anticancer drug in the nanoparticles; and (c) binding a peptide including an amino acid sequence of SEQ ID NO: 1 targeting brain cancer cells to the surface of the nanoparticles encapsulating the anticancer drug by a linker.

Hereinafter, the method of preparing nanoparticles according to the present disclosure will be described in detail for each step.

In the present disclosure, step (a) is a step of preparing porous silicon nanoparticles which are the basis of the nanoparticles for delivering a drug targeting brain cancer cells according to the present disclosure.

Figure 5:
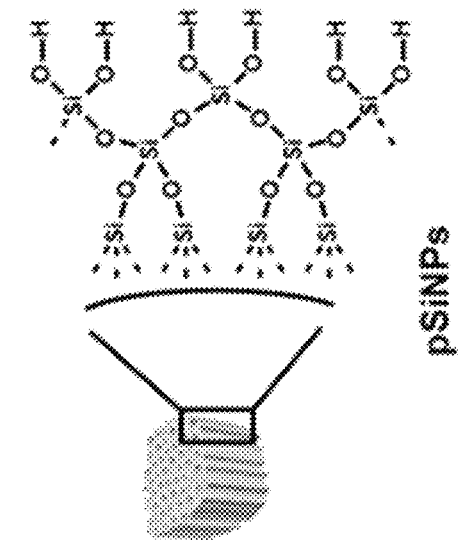
FIG. 5 is a schematic view showing a method of preparing porous silicon nanoparticles according to the present disclosure.
Figure 5:
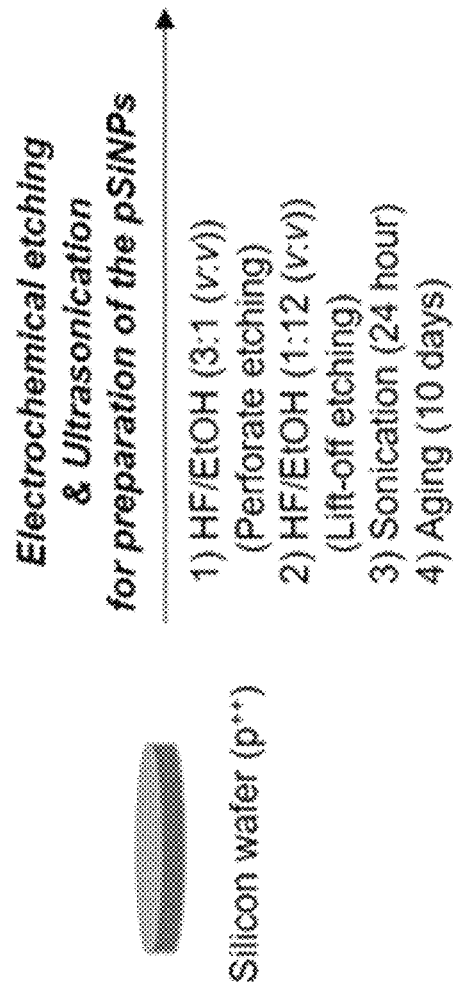

The porous silicon nanoparticles in step (a) may be prepared by preparing a porous silicon film using a silicon wafer, crushing the porous silicon film in an ultrasonic bath, and then filtering the crushed porous silicon film using a syringe filter, and Example 5 and FIG. 5 may be referenced for a more detailed preparation process.

The prepared porous silicon nanoparticles may have an average particle size of 100 to 200 nm, preferably 110 to 170 nm, and more preferably 139.7±18.8 nm, but the average particle size is not limited thereto.

In the present disclosure, step (b) is a step of encapsulating an anticancer drug in the porous silicon nanoparticles prepared in step (a).

The anticancer drug may be preferably 7-ethyl-10-hydroxy-camptothecin, but is not limited thereto, and it is possible to use other drugs capable of treating brain cancer targeted by the nanoparticles according to the present disclosure, particularly glioblastoma.

The step of encapsulating the anticancer drug in the porous silicon nanoparticles may be performed by uniformly dispersing the nanoparticles in ethanol using an ultrasonic bath, and then adding a solution in which the drug is dissolved to the dispersed nanoparticles, and then stirring the resulting mixture fora certain period of time, and removing the unencapsulated drug. The stirring may be performed using a vortex mixer for 24 hours, but is not limited thereto, and the stirring and drug removal process may be performed by those skilled in the art with appropriate adjustment.

In the present disclosure, step (c) is a step of binding a cell-penetrating peptide targeting brain cancer cells to the surface of nanoparticles loaded with the anticancer drug prepared in step (b).

Figure 7A:
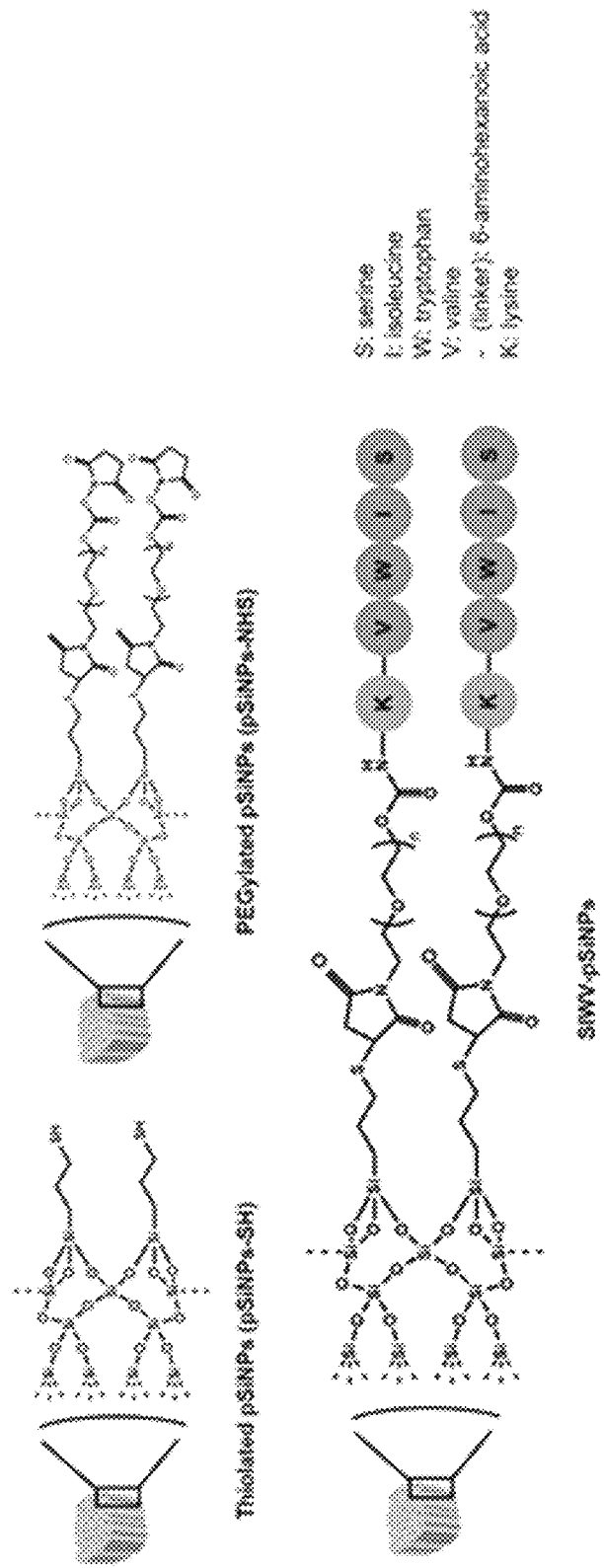
FIG. 7A shows a method of attaching an SIWV peptide to the surface of porous silicon nanoparticles and the sequence of the SIWV peptide.
Figure 7B:
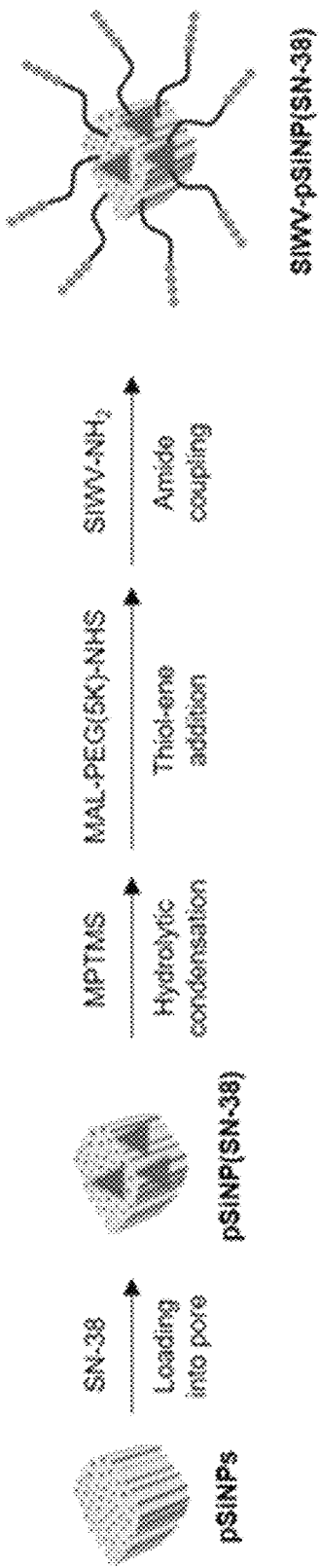
FIG. 7B shows a method of preparing porous silicon nanoparticles (SIWV-pSiNP(SN-38)) whose surface has been modified with an SIWV peptide and loaded with an SN-38 drug.

In the step of binding the peptide to the surface of the nanoparticles, porous silicon nanoparticles whose surface is modified with a peptide having an ability to target glioblastoma may be prepared by dispersing and mixing porous silicon nanoparticles and mercaptopropyl-triethoxysilane to make the surface end of the nanoparticles thiol groups, again dispersing the nanoparticles with the thiolated end in ethanol, adding maleimide-poly(ethylene glycol)-N-hydroxysuccinimide for mixing, and then adding distilled water in which the peptide was dissolved thereto, and culturing the resulting mixture, and a more specific method may be performed with reference to Example 7 and FIGS. 7A and 7B.

The peptide may be bound to porous silicon nanoparticles by a linker, and the linker may be polyethylene glycol, preferably maleimide-poly(ethylene glycol)-N-hydroxysuccinimide, and is not limited thereto.

Hereinafter, preferred examples for helping the understanding of the present disclosure will be suggested. However, the following examples are provided only to more easily understand the present disclosure, and the contents of the present disclosure are not limited by the following examples.

EXAMPLES

Example 1. Confirmation of Glioma Cell-Specific Uptake of Peptide Having SIWV Amino Acid Sequence The present inventors tried to investigate pathways through competitive treatment for clathrin, caveolae, macropinocytosis and dynamin, which are known intracellular uptake pathways in order to examine the intracellular uptake pathways of peptides with serine-isoleucine-tryptophan-valine (SIWV) amino acid sequences having cell permeability.

For this purpose, HeLa (human uterine cancer cells), U87MG (human primary glioblastoma cells), A549 (human lung cancer cells), and Huh7 (human liver cancer cells) cells were classified into a group in which those cells were each treated with an SIWV peptide, a group in which those cells were treated with 50 μM CPZ (chlorpromazine), which inhibits clathrin, for 30 minutes and treated with the SIWV peptide, a group in which those cells were treated with 1 mM methyl-beta-cyclodextrin (MβCD), which inhibits caveolae, for 30 minutes and treated with the SIWV peptide, a group in which those cells were treated with 50 μM ethyl isopropyl amiloride (EIPA), which inhibits macro-pinocytosis, for 30 minutes and treated with the SIWV peptide, and a group in which those cells were treated with 30 μg of dynasore, which inhibits dynamin, for 30 minutes and treated with the SIWV peptide, and treated with each material and peptide, and then the intracellular uptake pathways of SIWV were confirmed.

Figure 1B:
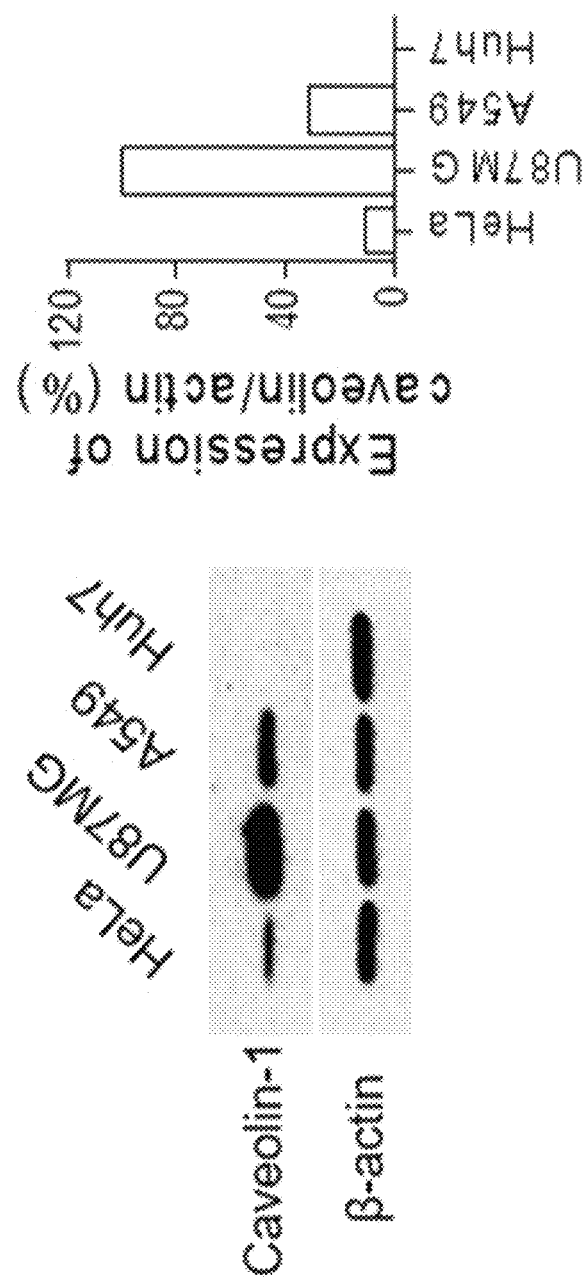
FIG. 1B shows the results of analyzing the expression level of a caveolin-1 protein in each of the four cancer cell lines from different tissue origins.

As a result, as illustrated in FIG. 1A, it was confirmed that the intracellular uptake of the SIWV peptide was specifically reduced in the group in which those cells were treated with MβCD which inhibits caveolae and treated with the SIWV peptide. Furthermore, as a result of measuring the caveolin-1 protein expression levels of the cell lines by performing western blotting, as can be seen in FIG. 1B, it was confirmed that U87MG cells expressed a remarkably high level of the caveolin-1 protein. Through this, it was confirmed that the SIWV peptide achieves intracellular uptake specific for U87MG cells in which caveolin is overexpressed using the caveolin receptor.

Example 2. Confirmation of In Vivo Distribution of Peptide Having SIWV Amino Acid Sequence In order to confirm the in vivo distribution of a peptide having the SIWV amino acid sequence, the present inventors labeled the SIWV peptide with tetramethylrhodamine (TAMRA) to enable visualization, and then injected the peptide into the tail veins of healthy mice, and observed the in vivo distribution of the SIWV peptide by a fluorescence signal.

Figure 2A:
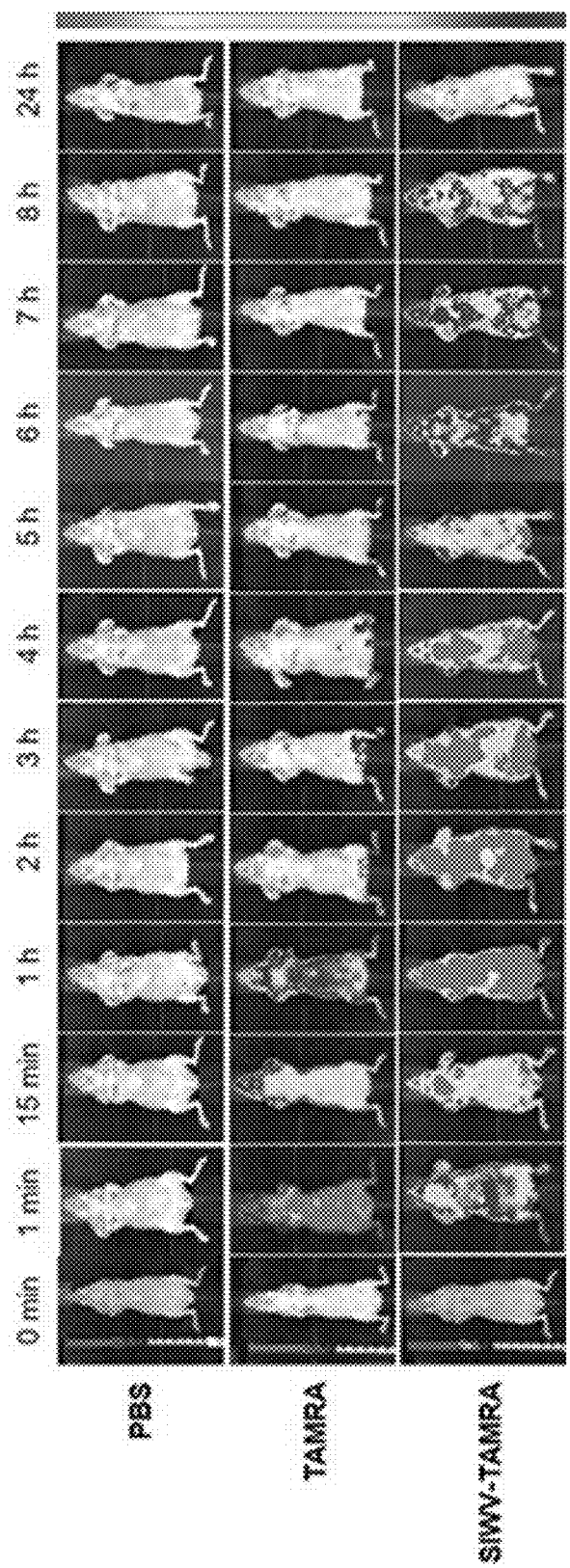
FIG. 2A shows the results of respectively injecting a SIWV peptide labeled with a fluorescent marker TAMRA (SIWV-TAMRA), a fluorescent label (TAMRA) and a phosphate-buffered saline (PBS buffer, PBS) into the tail veins of healthy mice, and then observing in vivo distribution by a fluorescence signal.

As a result, as illustrated in FIG. 2A, it was confirmed that a strong fluorescence signal was observed in most tissues including the brain within 1 hour and the SIWV peptide was excreted from the body after 24 hours. In contrast, it was confirmed that in the case of the control in which only TAMRA was injected, TAMRA spread throughout the mice within 1 minute and was excreted within 2 hours.

Figure 2B:
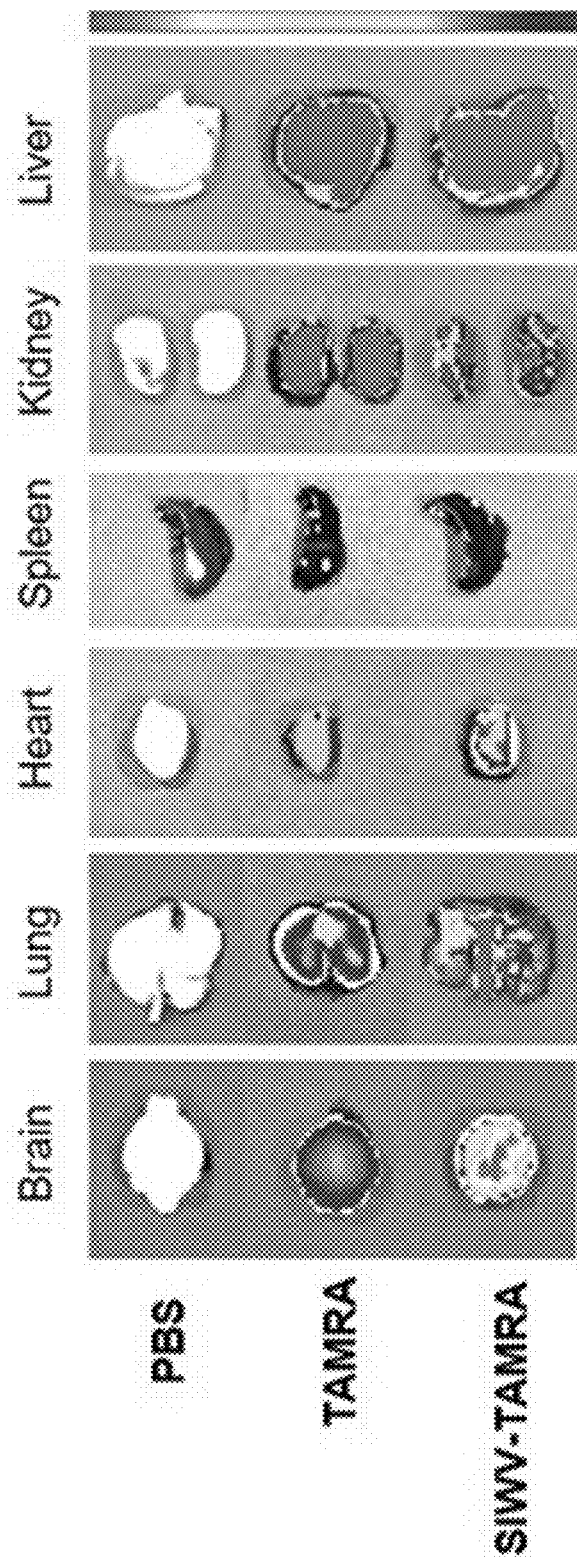
FIG. 2B shows the results of analyzing fluorescence intensity after removing the brain, the lungs, the heart, the spleen, the kidneys and the liver of the mice in each group of FIG. 2A.

In addition, the fluorescence intensity of each organ was analyzed 3 hours after injection of each peptide in order to confirm the tissue distribution of the SIWV peptide in vivo. As a result, as illustrated in FIG. 2B, it was confirmed that when the SIWV-TAMRA peptide was injected, fluorescence signals were detected in the brain, the lungs, the heart and the liver, and especially, a signal remarkably stronger than when only TAMRA was injected appeared in the brain.

Example 3. Confirmation of Passage of Peptide Having SIWV Amino Acid Sequence Through Blood-Brain Barrier In order to investigate whether the peptide having the SIWV amino acid sequence not only stays on the surface of the brain but also passes through the blood-brain barrier, the present inventors injected the SIWV-TAMRA peptide in the same manner as in the method of Example 2, removed the brain after 3 hours, and then froze the brain, and prepared a sample using a section of the frozen tissue to perform an analysis under a confocal microscope.

Figure 3:
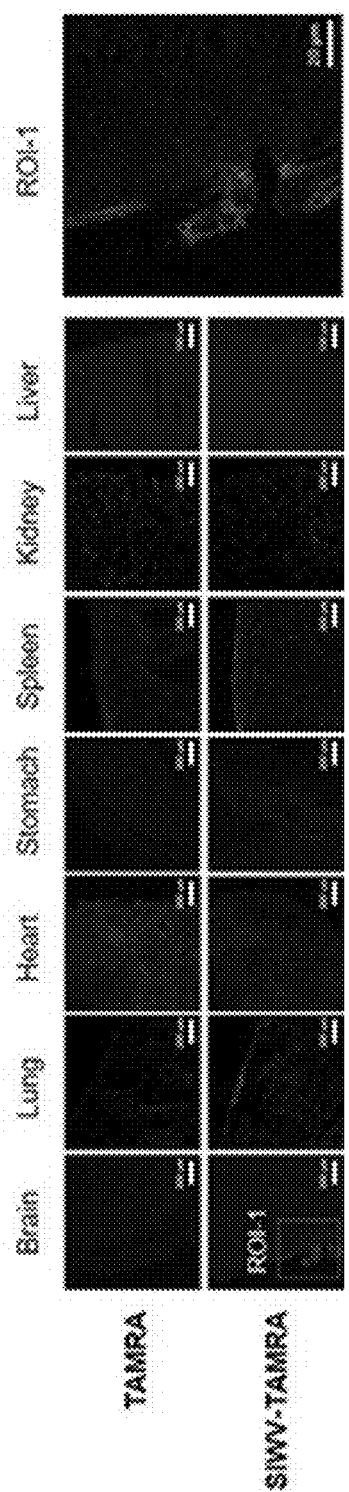
FIG. 3 shows the results of respectively injecting a SIWV peptide labeled with TAMRA (SIWV-TAMRA) and a fluorescent label (TAMRA) into the tail veins of mice, removing the brains, preparing tissue sections, and then observing the tissue sections under a confocal microscope, in order to examine the blood-brain barrier permeability of the SIWV peptide.

As a result, as illustrated in FIG. 3, it was confirmed that the SIWV peptide passed through the blood-brain barrier and was taken up by the brain.

Example 4. Confirmation of Ability of Peptide Having SIWV Amino Acid Sequence to Specifically Target Glioblastoma Based on the results of Example 3, the present inventors tried to investigate whether the peptide having the SIWV amino acid sequence passes through the blood-brain barrier and specifically targets glioblastoma. For this purpose, SIWV-TAMRA was injected into the tail vein of a glioblastoma mouse model, and the brain, the lungs, the heart, the spleen, the kidneys, and the liver were collected to analyze the fluorescence signals in each organ.

Figure 4:
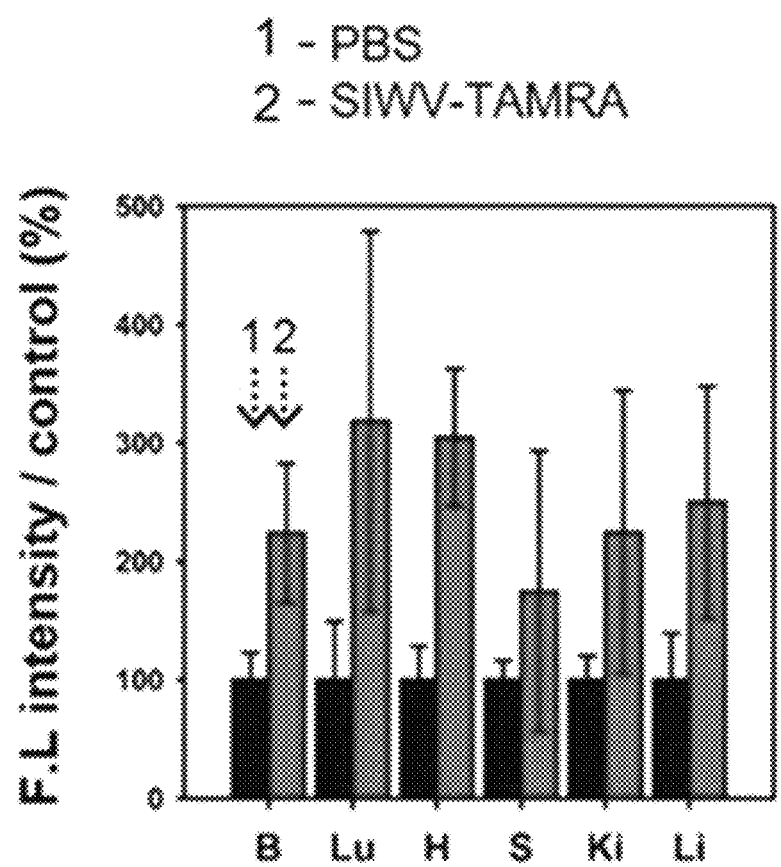
FIG. 4 shows the results of injecting the TAMRA-labeled SIWV peptide into the tail veins of glioblastoma model mice, removing the brain (B), the lungs (Lu), the heart (H), the spleen (S), the kidneys (Ki) and the liver (L), and then analyzing fluorescence intensity, in order to examine the ability of the SIWV peptide to specifically target glioblastoma.

As a result, as illustrated in FIG. 4, it was confirmed that the fluorescence intensities of SIWV-TAMRA were higher in the brain, the lungs, the heart, the kidneys, and the liver than in the control injected with PBS, and the fluorescence signal was 2-fold higher, especially in the brain site with glioblastoma, than the control.

Example 5. Preparation of Porous Silicon Nanoparticles

The present inventors prepared porous silicon nanoparticles having a particle size of about 140 nm by the following method, and FIG. 5 illustrates a schematic view of the preparation method.

Specifically, the porous silicon nanoparticles were prepared by an electrochemical etching method using a boron-doped p-type single crystal silicon wafer and an electrolyte solution in which 48% hydrofluoric acid and ethanol were mixed at a ratio of 3:1. Prior to preparing a porous silicon layer, the silicon wafer was anodized to form a thin porous layer, commonly called a sacrificial layer, in an electrolyte containing hydrofluoric acid, and then the resulting porous layer was treated with a 2M potassium hydroxide (KOH) solution to dissolve the porous layer. In order to prepare the porous silicon layer, the etching waveform consisted of a pulse with a current density of 46 mA/cm for 1.8 seconds and then a current density of 334 mA/cm for 0.4 seconds as one cycle. A porous silicon film with perforations at about every 200 nm was prepared by repeating this waveform for 150 cycles. Thereafter, the porous silicon film was collected from a silicon substrate by applying a current density of 3.1 mA/cm to a solution in which 48% hydrofluoric acid and ethanol were mixed at a ratio of 1:12 for 300 seconds. The collected porous silicon film and 6 mL of distilled water were put into a sealed vial, the resulting mixture was crushed using an ultrasonic bath for 24 hours, and then large particles were removed using a 0.22 μm syringe filter. The surface of the nanoparticles was formed of silicon hydroxide (Si—OH) by further culturing the porous silicon nanoparticles that had passed through the syringe filter at room temperature (25° C.) for 10 days. Thereafter, the nanoparticles were divided and moved into Eppendorf tubes (1.5 mL e-tube), and the tubes were subjected to 14000 rpm for 30 minutes using a centrifuge. Subsequently, the supernatant on the settled nanoparticles was removed, 1 mL of ethanol was added thereto, and the process of centrifugation and removal of the supernatant was repeated 3 times. The porous silicon nanoparticles prepared by the process were named pSiNPs.

Example 6. Preparation and Loading Efficiency Analysis of Porous Silicon Nanoparticles Loaded with 7-Ethyl-10-Hydroxy-Camptothecin Drug The present inventors tried to load the porous silicon nanoparticles produced in Example 5 with a glioblastoma therapeutic drug and analyze loading efficiency. For this purpose, after 1 mg of porous silicon nanoparticles were uniformly dispersed in 1.45 mL ethanol using an ultrasonic bath, 1 mg of a 7-ethyl-10-hydroxy-camptothecin drug (SN-38) dissolved in 50 μL of dimethyl sulfoxide (DMSO) was added to the dispersed porous silicon nanoparticles. And then the resulting mixture was stirred for 24 hours using a vortex mixer. After 24 hours, centrifugation was performed at 14000 rpm for 15 minutes to remove the unloaded SN-38, the supernatant on the settled nanoparticles was removed, and then add 1 mL of ethanol was further added thereto, and the process of centrifugation and removal of the supernatant was repeated 3 times.

Thereafter, in order to measure the loading efficiency of SN-38 in porous silicon nanoparticles, the supernatant was collected from each centrifugation step and SN-38 fluorescence intensity was measured using a spectro-fluorophotometer manufactured by SHIMADZU, and then the loading efficiency was analyzed by comparing the fluorescence intensity with a standard curve. In this case, a standard quartz cell having a thickness of 1 cm was used as a cell used for the measurement.

Figure 6:
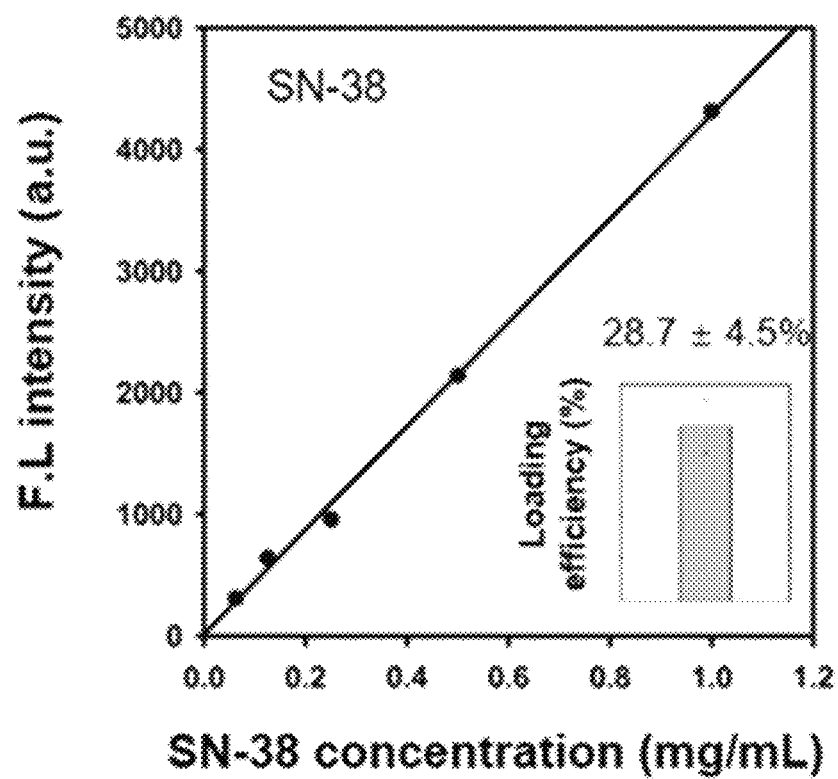
FIG. 6 shows the results of measuring the loading efficiency of an SN-38 drug in the prepared porous silicon nanoparticles.

As a result of the analysis, as illustrated in FIG. 6, it was found that the loading efficiency of SN-38 was 28.7±4.5%, and the present inventors named the SN-38 drug-loaded porous silicon nanoparticles pSiNP(SN-38).

Example 7. Attachment of SIWV Peptide to Surface of pSiNP(SN-38)

The present inventors tried to attach an SIWV peptide that had been confirmed to have an ability to pass through the blood-brain barrier and specifically target glioblastoma through Examples 3 and 4 to the porous silicon nanoparticles (pSiNP(SN-38)) loaded with the SN-38 drug prepared in Example 6.

The surface modification method and schematic view of the porous silicon nanoparticles for attaching the SIWV peptide to the surface are illustrated in FIGS. 7A and 7B. Specifically, 1 mg of pSiNP(SN-38) and 3-mercaptopropyl-triethoxysilane were dispersed in 1 mL of ethanol, and then the resulting dispersion was mixed at room temperature (25°

C.) for 4 hours using a vortex mixer. In order to remove the remaining 3-mercaptopropyl-triethoxysilane, the process of adding ethanol thereto, centrifugation at 14000 rpm for 15 minutes and washing was repeated 3 times. Next, nanoparticles whose surface ends were thiol by 3-mercaptopropyl-triethoxysilane were dispersed in 800 μL of ethanol, and then 1 mg of maleimide (MAL)-poly(ethyleneglycol (PEG)-N-hydroxysuccinimide (NHS) dissolved in 200 μL of ethanol was added thereto, and the resulting mixture was mixed at room temperature for 2 hours using a vortex mixer. Thereafter, the remaining MAL-PEG-NHS was removed by adding ethanol thereto and repeating the process of centrifugation at 14,000 rpm for 15 minutes. Subsequently, the remaining particles were re-dispersed in 100 μL of ethanol, 0.2 mg of the SIWV peptide dissolved in 100 μL of ethanol was added to attach the SIWV peptide, and the resulting mixture was cultured in a refrigerator at 4° C. for 4 hours. After 4 hours, the remaining particles after washing were dispersed in 10 μL of distilled water by repeating the process of adding distilled water thereto and centrifugation at 14000 rpm for 15 minutes three times, and stored at 4° C.

The present inventors named the porous silicon nanoparticles whose surface prepared by the process was modified with the SIWV peptide and loaded with the SN-38 drug SIWV-pSiNP(SN-38).

Example 8. Analysis of Characteristics of Prepared Nanoparticles 8-1. Confirmation of Size and Zeta Potential of Each Nanoparticle The present inventors used Zetasizer Nano ZS90 manufactured by Malvern Instruments, Inc. in order to measure the hydrodynamic size and zeta potential of pSiNPs, pSiNP (SN-38) and SIWV-pSiNP(SN-38) nanoparticles prepared in Examples 5 to 7, respectively.

Figure 8A:
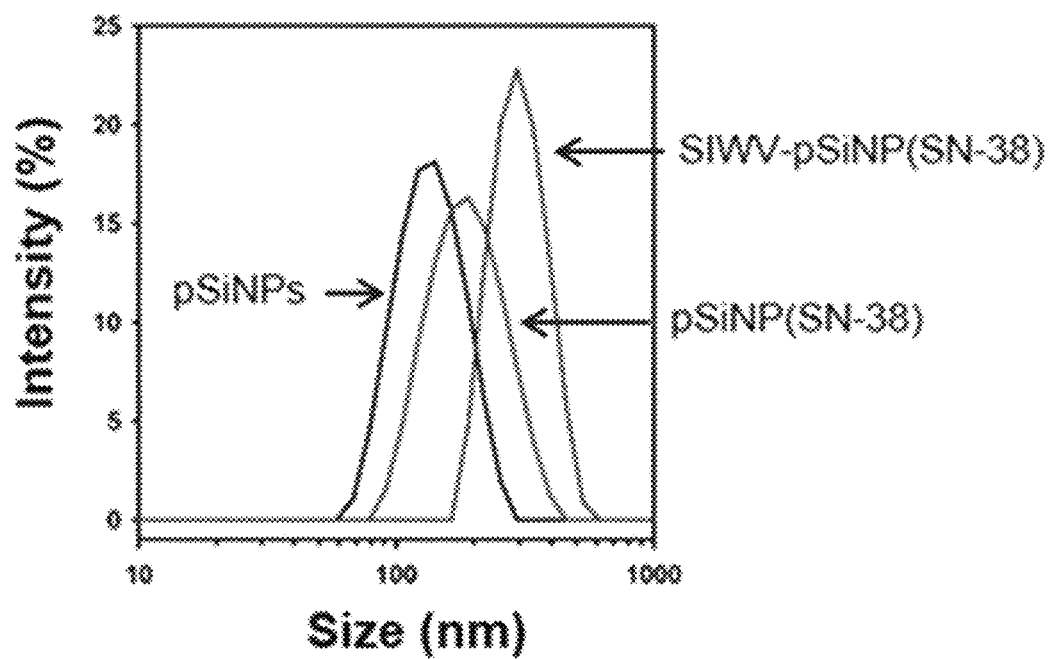
FIG. 8A shows the results of measuring the hydrodynamic sizes of porous silicon nanoparticles (pSiNPs), SN-38 drug-loaded porous silicon nanoparticles (pSiNP(SN-38)) and porous silicon nanoparticles whose surface has been modified with an SIWV peptide and loaded with an SN-38 drug (SIWV-pSiNP(SN-38)).
Figure 8B:
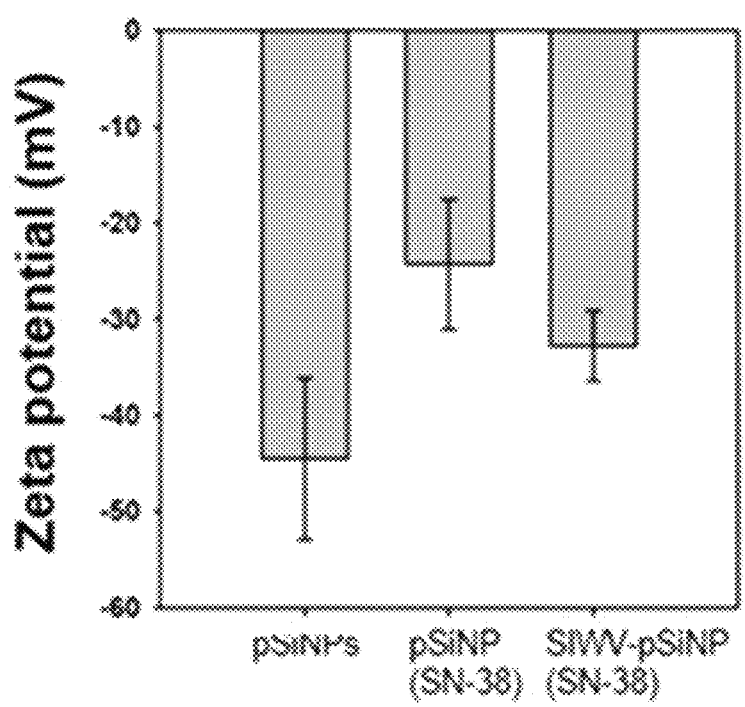
FIG. 8B shows the results of measuring the zeta potential of porous silicon nanoparticles (pSiNPs), SN-38 drug-loaded porous silicon nanoparticles (pSiNP(SN-38)) and porous silicon nanoparticles whose surface has been modified with an SIWV peptide and loaded with an SN-38 drug (SIWV-pSiNP(SN-38)).

As a result of measuring the hydrodynamic size and zeta potential of each nanoparticle, as illustrated in FIGS. 8A and 8B, it was found that the pSiNPs had a hydrodynamic diameter of 139.7±18.8 nm in diameter and a zeta potential of −44.5±8.39 mV, and it was found that the pSiNP(SN-38) nanoparticles had a negative surface charge decreased to −24.3±6.73 mV and a slight increase in diameter to 196.3±32.2 nm. In the case of SIWV-pSiNP(SN-38) nanoparticles, the size was further increased to 306.2±32.7 nm due to the attachment of the cell-penetrating peptide, and the zeta potential was measured to be −34.8±5.91 mV.

8-2. Transmission Electron Microscopic Observation of Each Nanoparticle

Figure 9:
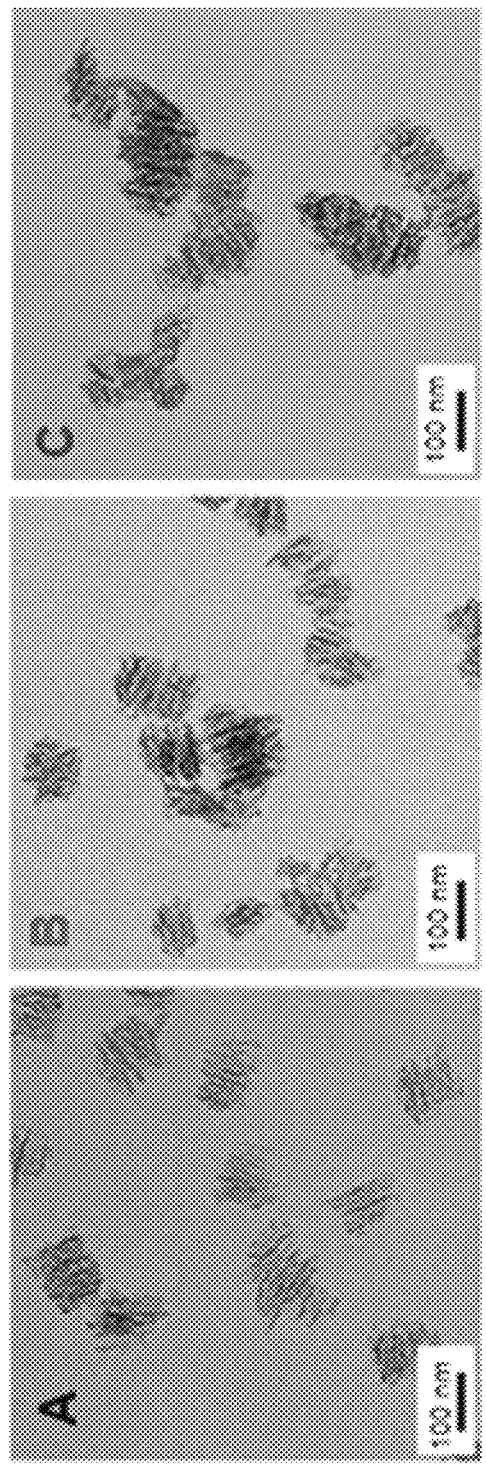
FIG. 9 shows transmission electron microscope photographs for each of the pSiNPs, pSiNP(SN-38) and SIWV-pSiNP(SN-38) nanoparticles.

Next, in order to observe the morphology of pSiNPs, pSiNP(SN-38) and SIWV-pSiNP(SN-38) nanoparticles using a transmission electron microscope, the present inventors photographed each nanoparticle with a Tecnai transmission electron microscope manufactured by FEI Co., and the results are illustrated in FIG. 9.

As a result of observation, it could be confirmed that pSiNPs nanoparticles had a relatively uniform particle size and a porous structure, and these properties were maintained after the SN-38 drug was loaded and even after the cell-penetrating peptide was later attached thereto.

8-3. Confirmation of Surface of Each Nanoparticle

The present inventors confirmed the functional group on the surface of each of pSiNPs, pSiNP(SN-38) and SIWV-pSiNP(SN-38) nanoparticles using attenuated total reflection Fourier transform infrared (FT-IR) spectroscopy manufactured by Thermo Fisher Scientific in order to confirm the result of loading the SN-38 drug into the porous silicon nanoparticles and the attachment of the SIWV peptide.

Figure 10:
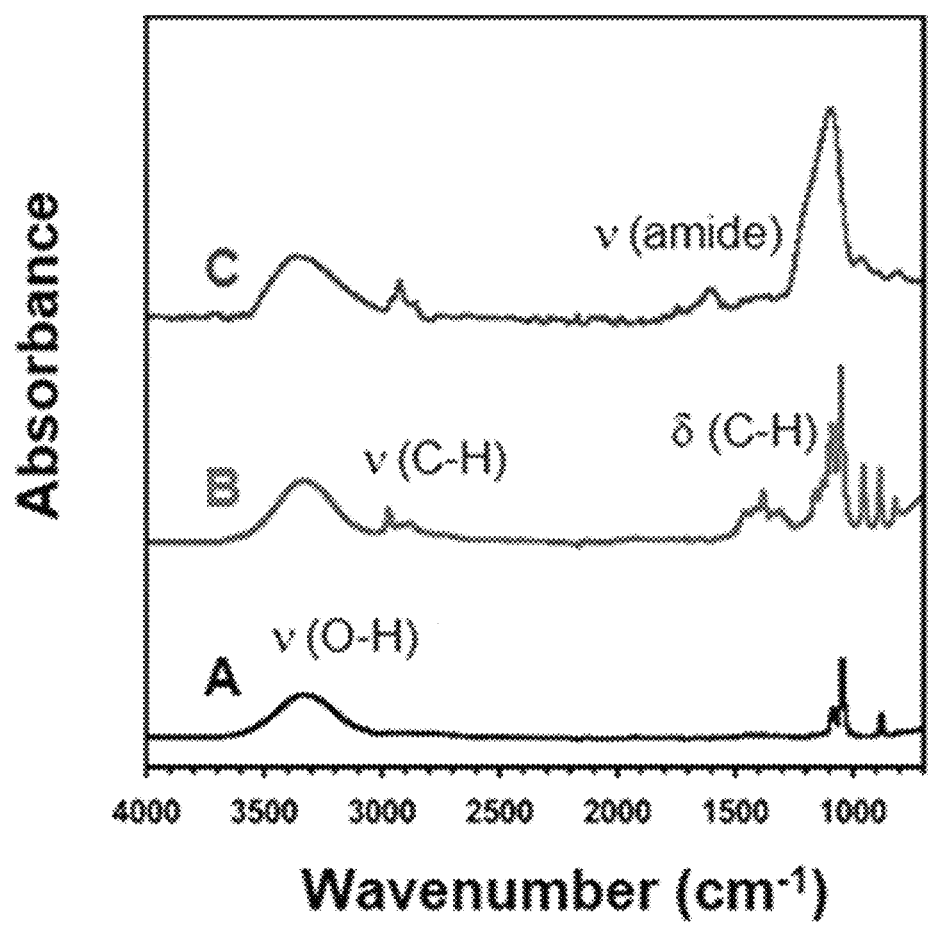
FIG. 10 shows the results of analyzing surface functional groups using FT-IR for each of pSiNPs, pSiNP(SN-38) and SIWV-pSiNP(SN-38) nanoparticles.

As a result, as illustrated in FIG. 10, it was confirmed that pSiNPs showed a v(O—H) functional group at 3550 to 3200 cm$^{-1}$ and v(Si—O) stretching at 1065 cm$^{-1}$. In the case of pSiNP(SN-38) loaded with the SN-38 drug, it could be seen that the pSiNP(SN-38) nanoparticles were loaded with the SN-38 drug by confirming (C—H) stretching and bending vibrations of the SN-38 drug at 2950 to 2860 cm$^{-1}$ and 1480 to 1350 cm$^{-1}$, respectively. It was confirmed that after the SIWV peptide was attached, the SIWV peptide was attached by confirming a v(amide) functional group at 1650 cm$^{-1}$.

Example 9. Confirmation of Release Behavior of SIWV-pSiNP(SN-38) Nanoparticles

The present inventor tried to confirm the release behavior of the SN-38 drug loaded into SIWV-pSiNP(SN-38) nanoparticles in phosphate-buffered saline (PBS). For this purpose, 0.1 mg of SIWV-pSiNP(SN-38) nanoparticles were dispersed in 1 mL of PBS and then cultured at 37° C. After a certain period of time, the nanoparticles and the supernatant were separated by centrifugation at 14,000 rpm for 15 minutes, and then the separated supernatant was irradiated with an excitation wavelength of 367 nm, and an emission wavelength at 561 nm was measured.

Figure 11:
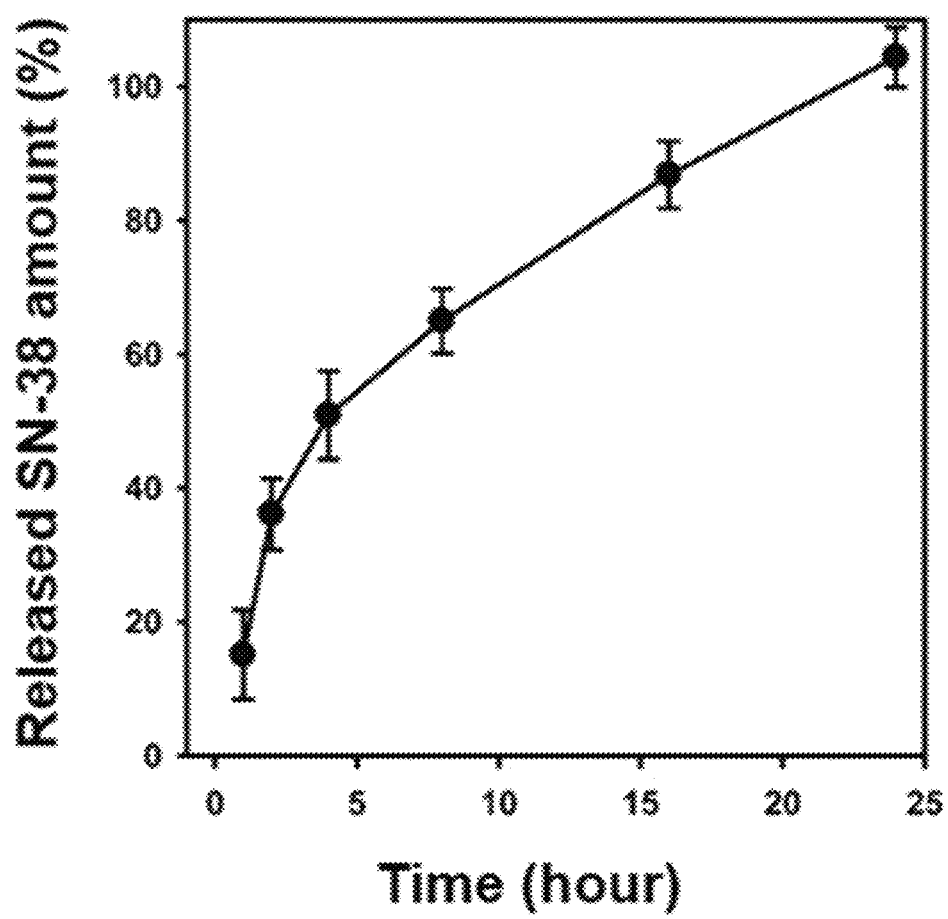
FIG. 11 shows the results of measuring the release behavior of the SN-38 drug loaded inside the SIWV-pSiNP(SN-38) nanoparticles in PBS.

As a result, as illustrated in FIG. 11, it was confirmed that the SN-38 drug loaded in the SIWV-pSiNP(SN-38) nanoparticles was mostly released within 2 hours, and the remaining drug was gradually released for 24 hours.

Example 10. Verification of Intracellular Uptake and Cytotoxicity of SIWV-pSiNP(SN-38) Nanoparticles The present inventor conducted the following experiments to confirm the intracellular uptake efficiency and cytotoxicity of SIWV-pSiNP(SN-38). Specifically, U87MG cells were seeded into 96-well plates at a density of 10,000 cells/well and cultured under the conditions of 5% $CO_2$ and 37° C. for 24 hours. Thereafter, the cells were treated with 100 μL of each of the SN-38 drug alone, pSiNPs, pSiNP (SN-38) and SIWV-pSiNP(SN-38) nanoparticles at a concentration of 6.25, 12.5, 25, 50, and 100 μM, respectively, and cultured for 6 hours. After 6 hours, in order to confirm the intracellular uptake efficiency, cell nuclei were stained by treating the cells with a 4',6-diamino-2-phenylindole (DAPI) reagent for 10 minutes, and cell membranes were then stained by treating the cells with a CellMask™ Deep Red Plasma membrane stain reagent for 1 hour. After staining, the cells were washed three times with PBS and treated with 4% paraformaldehyde for 20 minutes to fix the cells, and then the cells were observed under a confocal microscope. A blue wavelength image was observed at an excitation wavelength of 405 nm and an emission wavelength of 410 to 450 nm, a green wavelength image was observed at an excitation wavelength of 405 nm and an emission wavelength of 505 to 545 nm, and a red wavelength image was observed at an excitation wavelength of 640 nm and an emission wavelength of 650 to 690 nm.

Figure 12:
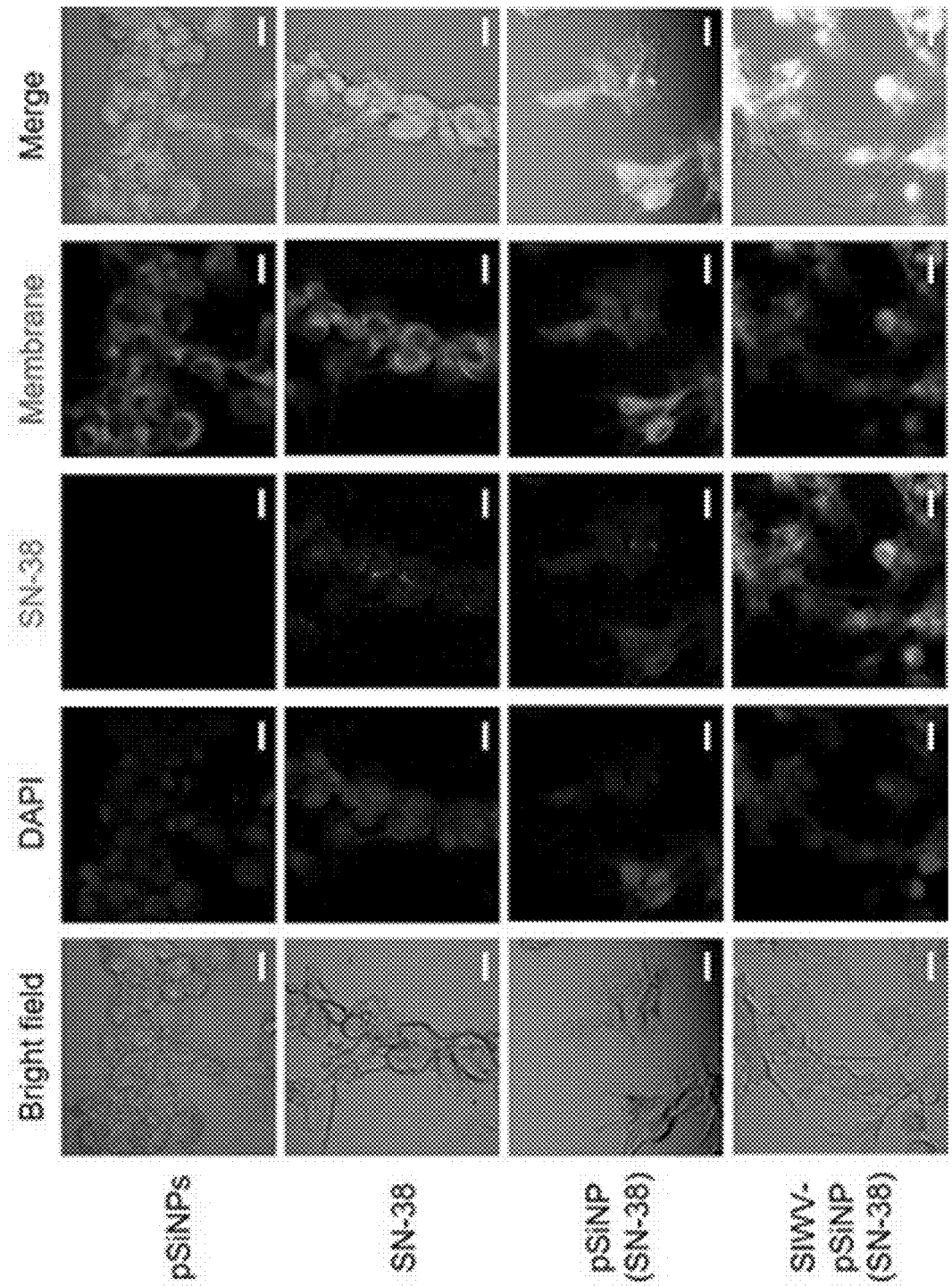
FIG. 12 shows the results of treating U87MG cells with each of the materials and observing the treated U87MG cells under a confocal microscope in order to analyze the intracellular uptake efficiencies of pSiNPs, an SN-38 drug, pSiNP(SN-38) and SIWV-pSiNP(SN-38) nanoparticles.

As a result, as illustrated in FIG. 12, it could be confirmed that in the case of the pSiNP, SN-38, pSiNP(SN-38) treatment groups to which the SIWV peptide was not attached, intracellular uptake did not occur even after culturing for 6 hours, whereas in the case of the SIWV-pSiNP(SN-38) group to which the SIWV peptide was attached, effective uptake occurred in U87MG cells under the given conditions and the SN-3 drug was delivered and released.

Meanwhile, after the cells were treated with SN-38 and each of the nanoparticles as described above and cultured for 6 hours, 10 μL of a 10% WST-1 reagent was added to each well and the cells were cultured for 2 hours. Thereafter, cell viability was analyzed by measuring the absorbance at 450 nm using a microplate reader, and the cell viability was analyzed using a relative percentage for U87MG cells not treated with nanoparticles.

Figure 13:
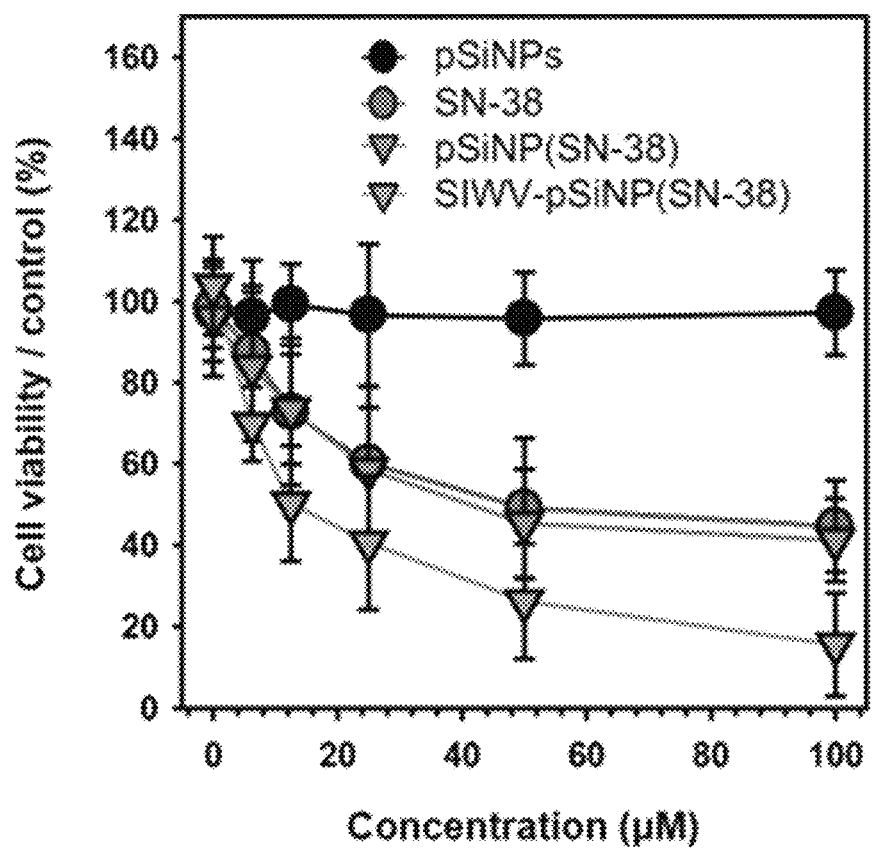
FIG. 13 shows the results of analyzing the degree of cytotoxicity by treating U87MG cells with each of pSiNPs, an SN-38 drug, pSiNP(SN-38) and SIWV-pSiNP(SN-38) nanoparticles at various concentrations and measuring the cell viability.

As a result, as illustrated in FIG. 13, it was found that a group in which cells were treated with pSiNPs showed no toxicity even after the cells were cultured for 6 hours, whereas groups in which cells were treated with SN-38, pSiNPs, pSiNP(SN-38) and SIWV-pSiNP(SN-38) had increased toxicity as the treatment concentration was increased. When the cells were treated with SIWV-pSiNP (SN-38) at a low concentration of 6.5 μM, the toxicity of U87MG cells was 31.2%, showing a significantly higher cytotoxicity than the groups in which the cells were treated with SN-38 (12.4%) and pSiNP(SN-38) (16.2%). In addition, it could be seen that even at a high concentration of 100 μM, the cytotoxicity of the group in which the cells were treated with SIWV-pSiNP(SN-38) was 84.4%, which is higher cytotoxicity than those of the SN-38 group (55.4%) and the pSiNP(SN-38) group (58.8%).

Example 11. Confirmation of In Vivo Distribution of SIWV-pSiNP(SN-38) Nanoparticles in Glioblastoma Mouse Model In order to confirm the in vivo distribution of SIWV-pSiNP(SN-38) nanoparticles in a glioblastoma mouse model, the present inventor injected each of the pSiNP, pSiNP(SN-38) and SIWV-pSiNP(SN-38) nanoparticles into the tail veins of the mice, and then observed the in vivo distribution of the nanoparticles using IVIS.

More specifically, 7-week-old female ICR mice were used, and the mice were bred in a 12-hour light/dark cycle under conditions of an ambient temperature of 23±1° C. and a relative humidity of 60±10%. Thereafter, in order to produce a glioblastoma model mouse, a glioblastoma model mouse was produced by anesthetizing the mouse with tribromoethanol, placing the anesthetized mouse in a stereotaxic apparatus, and then injecting 1,000,000 U87MG cells into each mouse according to the following coordinates (anteroposterior: −3.0 mm from bregma; mediolateral: 1.8 mm from bregma; dorsoventral direction: −3.0 mm from skull bregma). Two weeks after transplanting U87MG cells, the mice were randomly classified into four groups as follows: (1) Control (PBS intravenous injection), (2) pSiNP group (20 mg/kg pSiNP intravenous injection), (3) pSiNP (SN-38) group (20 mg/kg pSiNP(SN-38) intravenous injection), and (4) SIWV-pSiNP(SN-38) group (20 mg/kg SIWV-pSiNP(SN-38) intravenous injection). The corresponding nanoparticles were injected into the tail veins of the mice of each group, and after 2 hours, the mice were anesthetized with tribromoethanol, perfused with PBS, and then fixed with 4% paraformaldehyde. Subsequently, the brain, the lungs, the heart, the spleen, the kidneys, and the liver were removed from the mice, and each organ was immersed in a buffer of pH 12 for 1 hour, and then the in vivo distribution of nanoparticles was confirmed by measuring the fluorescence intensity in each organ using a Xenogen IVIS 200 luminescence and fluorescence animal imaging system. As an excitation wavelength, 445 to 490 nm was used, and as a fluorescence emission wavelength, 530 to 590 nm was used.

Figure 14A:
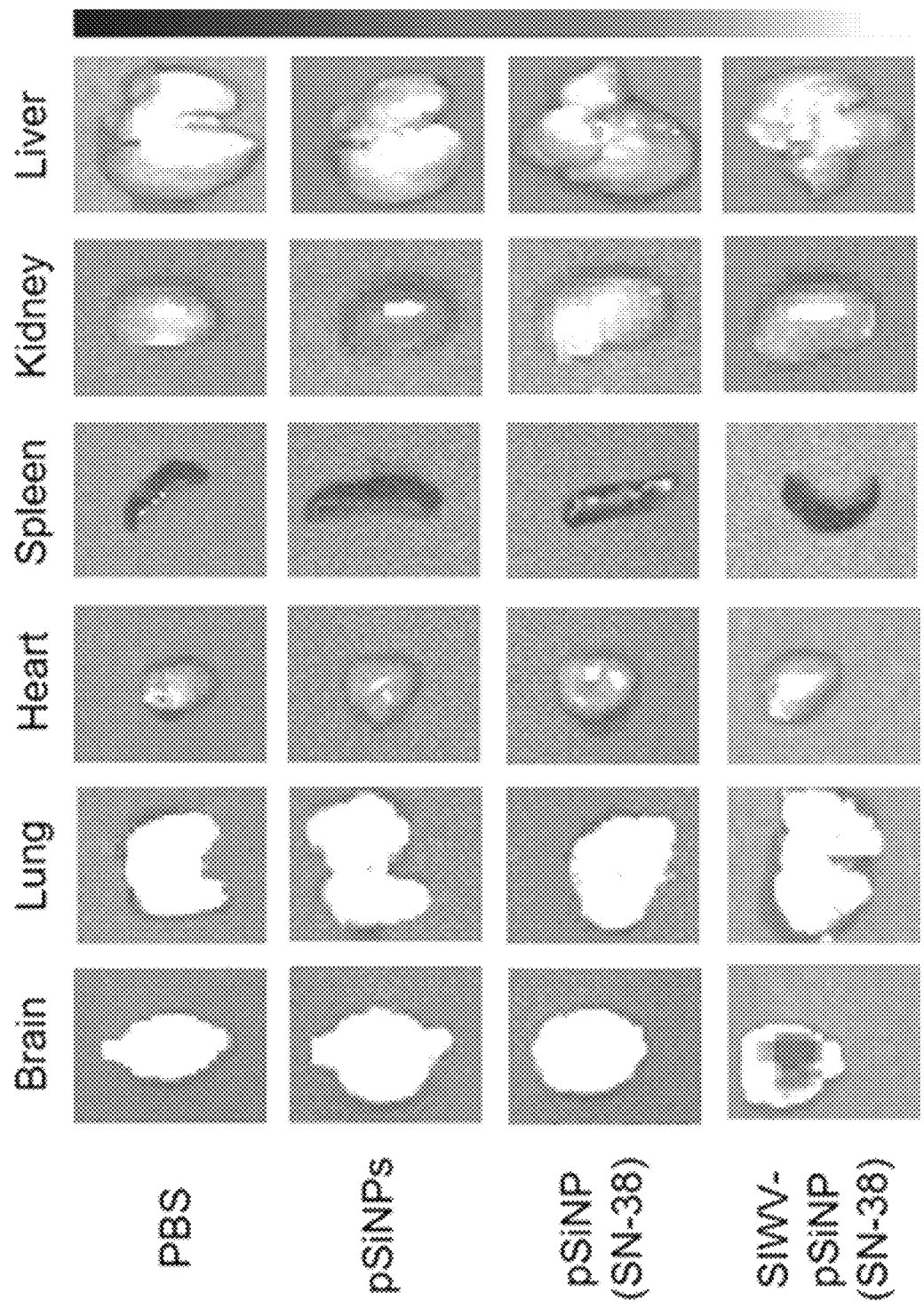
FIG. 14A shows the results of observing the in vivo distribution of each of the nanoparticles by injecting each of PBS, pSiNPs, pSiNP(SN-38) and SIWV-pSiNP(SN-38) nanoparticles into the tail veins of glioblastoma model mice and removing the brain, the lungs, the heart, the spleen, the kidneys, and the liver after 2 hours to measure fluorescence intensity.
Figure 14B:
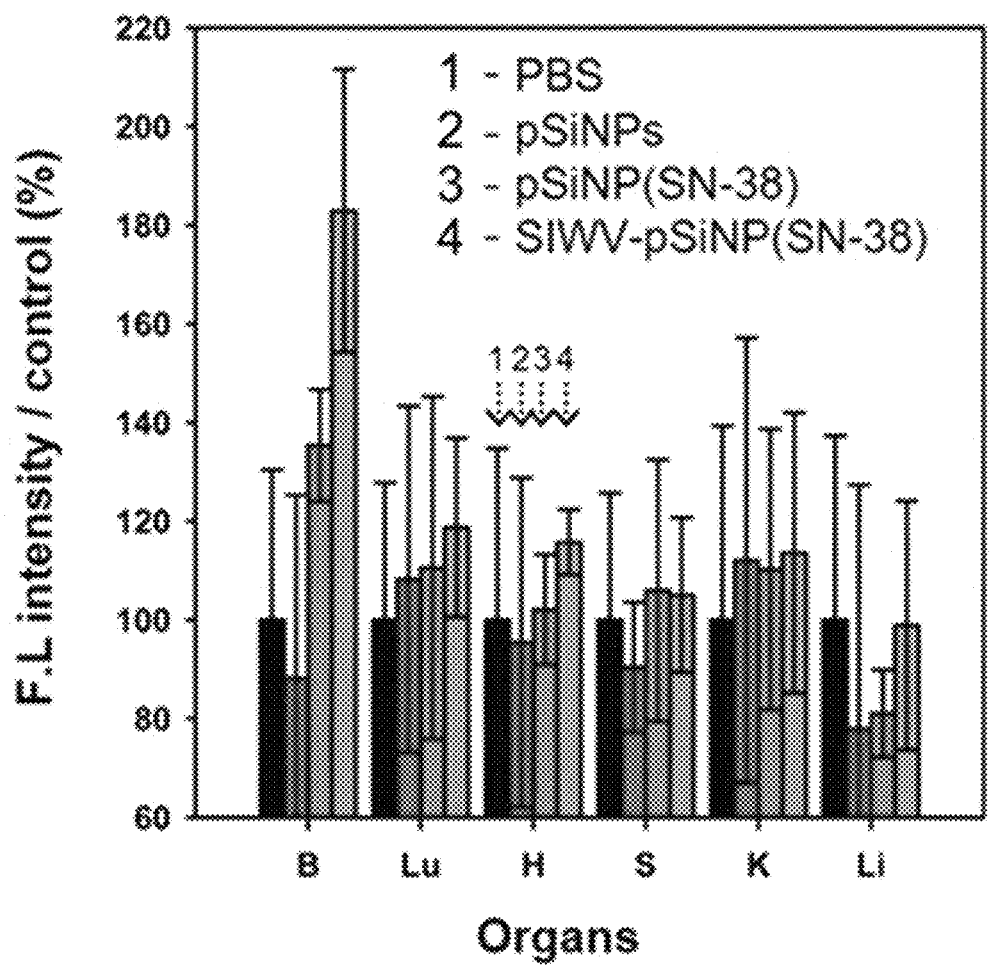
FIG. 14B shows the results of quantifying the fluorescence intensity values in FIG. 14A, and then comparing the values.
Figure 15A:
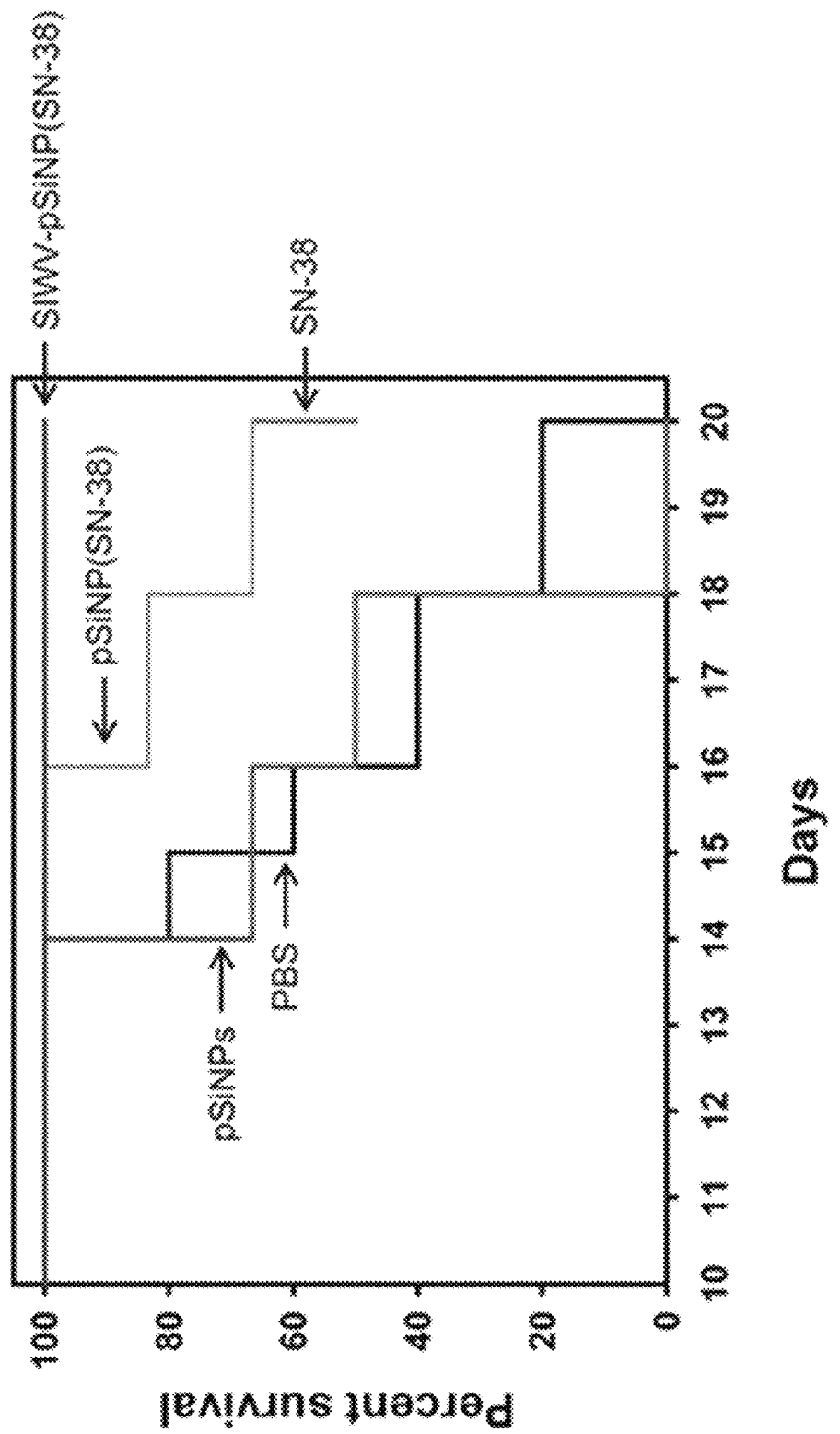
FIGS. 15A and 15B show the results of transplanting U87MG cells into mice, and injecting each of PBS, pSiNPs, an SN-38 drug, pSiNP(SN-38) and SIWV-pSiNP(SN-38) nanoparticles into the tail veins of the mice, and then measuring the viability and body weight of each mouse until day 20.
Figure 15B:
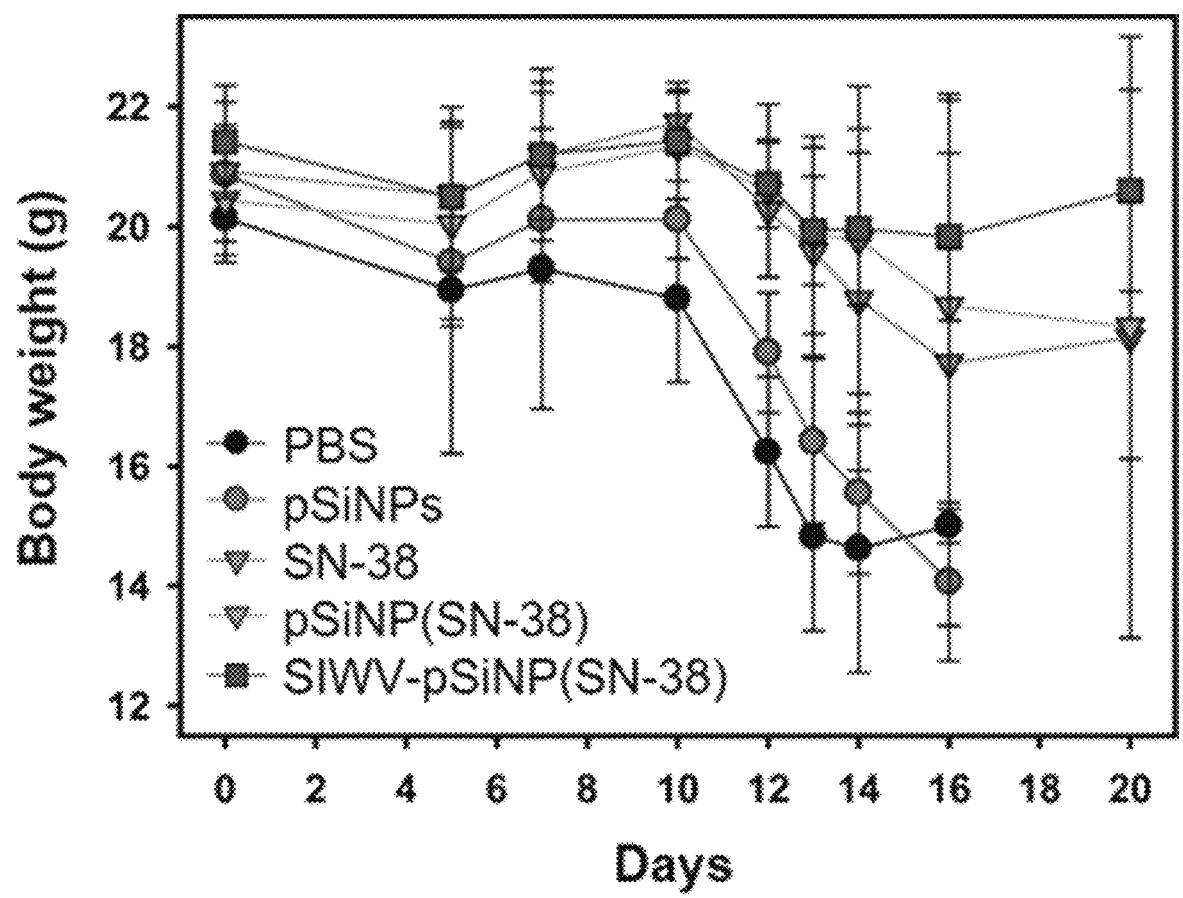
Figure 15C:
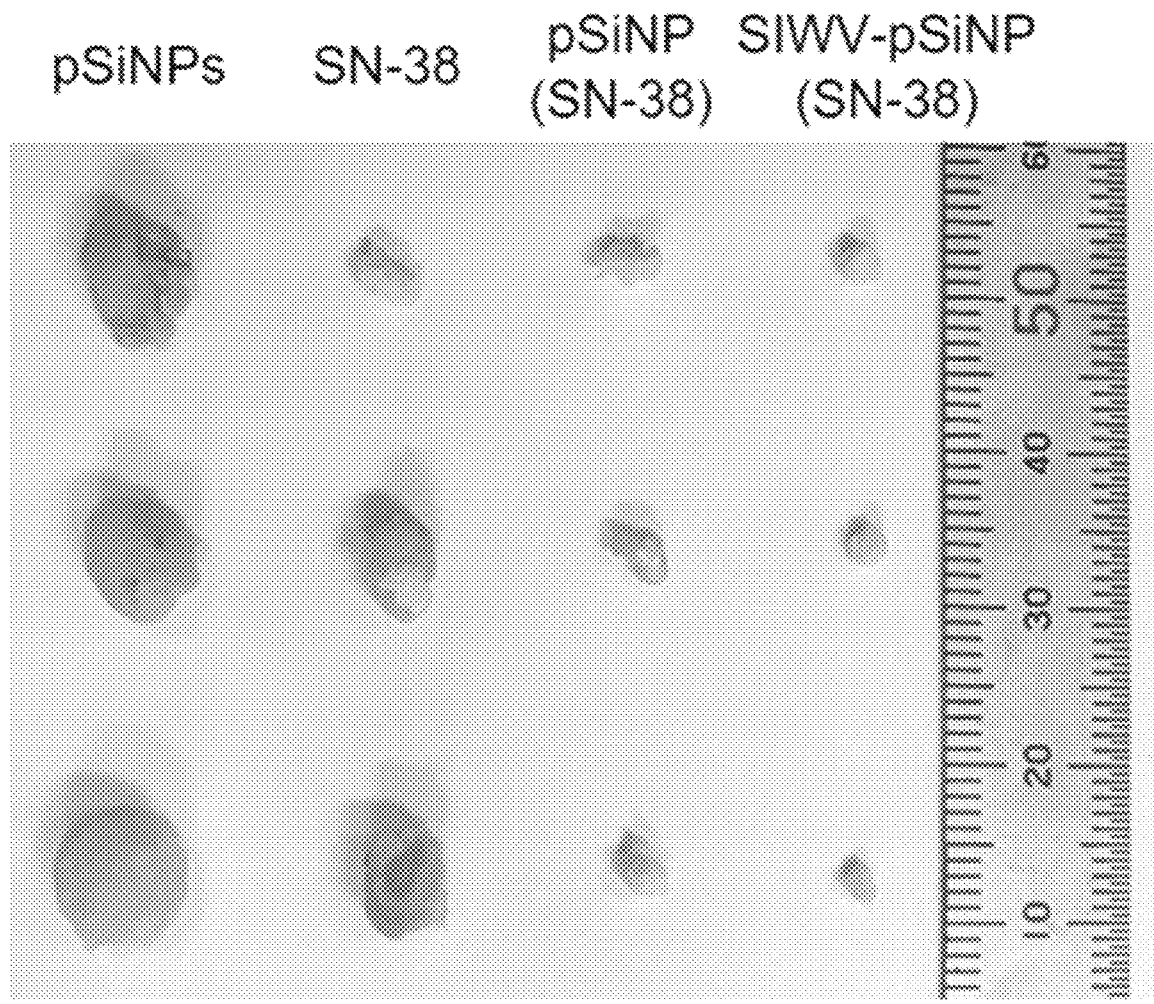
FIG. 15C shows the results of removing a glioblastoma tumor from the mice of each group on day 20, and then measuring the size of the tumor.
Figure 15D:
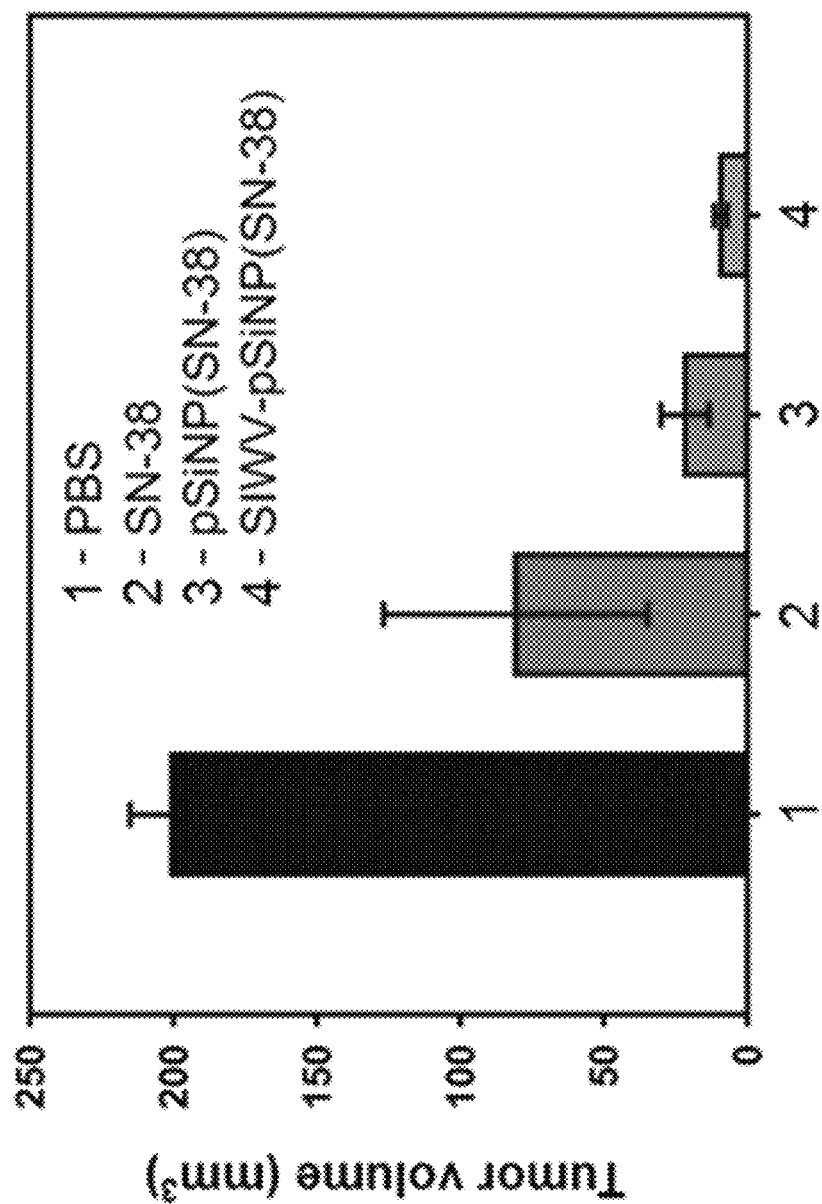
FIG. 15D shows the results of removing the glioblastoma tumor from the mice of each group on day 20, and then measuring the volume of the tumor.

As a result, as illustrated in FIGS. 14A and 14B, in the case of the group injected with SIWV-pSiNP(SN-38), a strong fluorescence signal could be confirmed in the brain.

Example 12. Confirmation of Therapeutic Effect of SIWV-pSiNP(SN-38) Nanoparticles in Glioblastoma Mouse Model The present inventors tried to confirm the substantive therapeutic effect of SIWV-pSiNP(SN-38) nanoparticles in a glioblastoma mouse model.

For this purpose, mice with glioblastoma were classified into the following five groups (number of mice per group=6), and the body weight and number of mice were measured at an interval of 2 to 3 days. (1) Control (PBS intravenous injection), (2) pSiNP group (20 mg/kg pSiNP intravenous injection), (3) SN-38 group (SN-38 drug intravenous injection), (4) pSiNP(SN-38) group (20 mg/kg pSiNP(SN-38) intravenous injection) (5) SIWV-pSiNP(SN-38) group (20 mg/kg SIWV-pSiNP(SN-38) intravenous injection). The nanoparticles corresponding to each of the groups were injected into the tail vein on days 14, 15, 16, and 18 after the U87MG cells were transplanted, and finally the remaining glioblastoma mice were euthanized on day 20, and tumor size and volume were measured using calipers.

As a result, as illustrated in 15A to 15D, it was confirmed that in the case of the SIWV-pSiNP(SN-38) group compared to the other groups, the survival rate of the mice was high, no weight loss appeared, and the size and volume of the tumor were remarkably decreased. From the above results, it could be seen that SIWV-pSiNP(SN-38) had an excellent therapeutic effect on glioblastoma.

Figure 16:
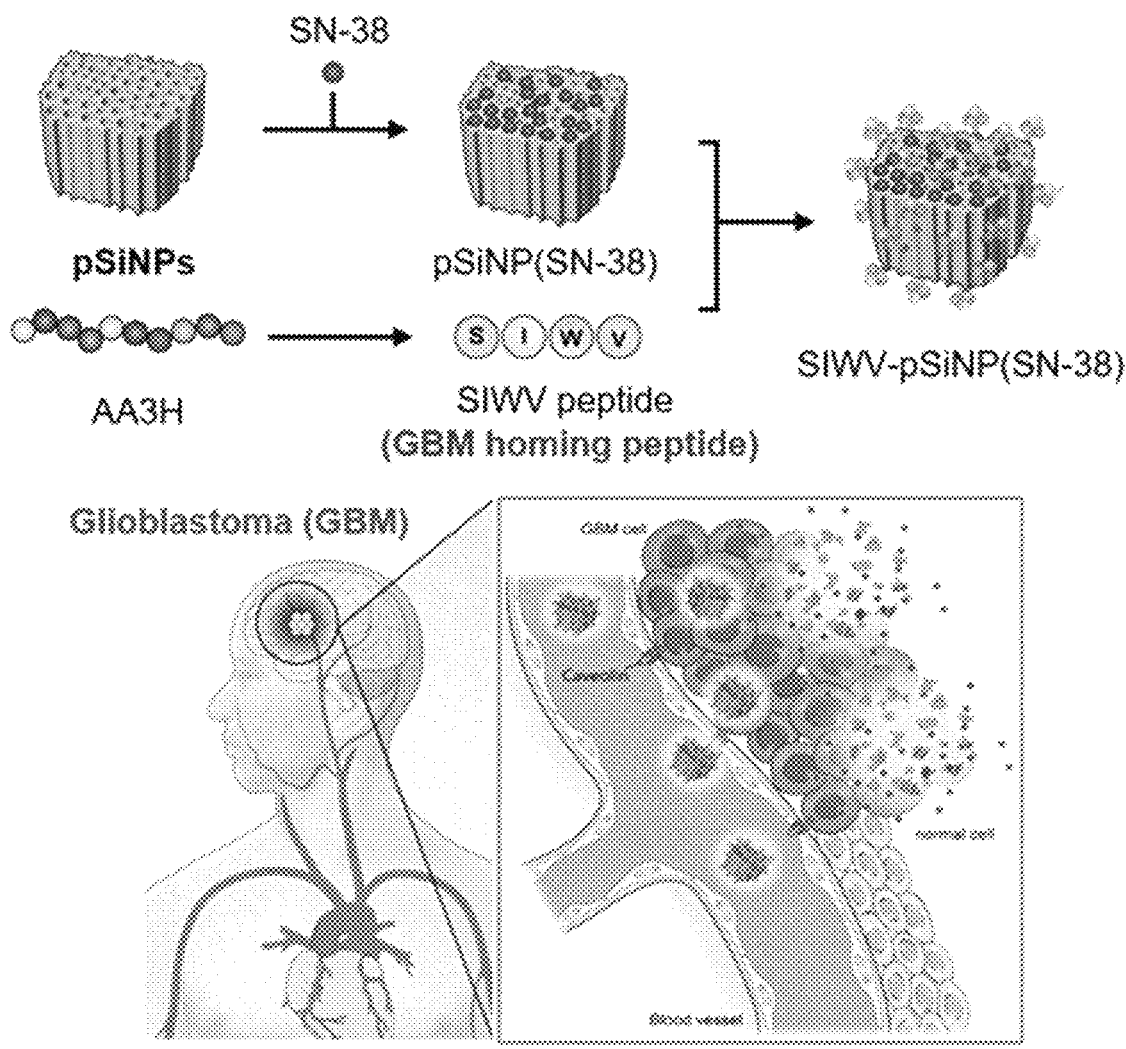
FIG. 16 shows a method of preparing porous silicon nanoparticles (SIWV-pSiNP(SN-38)) in which the SN-38 drug according to the present disclosure is loaded and whose surface binds to an SIWV peptide, and a glioblastoma-specific anticancer effect thereof.

In conclusion, a method of preparing porous silicon nanoparticles (SIWV-pSiNP(SN-38)) into which the SN-38 drug according to the present disclosure is loaded and whose surface binds to an SIWV peptide, and a glioblastoma-specific anticancer effect thereof are illustrated in FIG. 16.

The above-described description of the present disclosure is provided for illustrative purposes, and those skilled in the art to which the present disclosure pertains will understand that the present disclosure can be easily modified into other specific forms without changing the technical spirit or essential features of the present disclosure. Therefore, it should be understood that the above-described embodiments are only exemplary in all aspects and are not restrictive.

INDUSTRIAL APPLICABILITY

It was confirmed that the nanoparticles according to the present disclosure can be used as an effective drug delivery system for the treatment of glioblastoma by inducing a more efficient therapeutic effect on glioblastoma, so that the nanoparticles according to the present disclosure are expected to be usefully utilized in the fields of anticancer research and anticancer drug development.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. Nanoparticles for delivering a drug targeting brain cancer cells, comprising: (i) porous silicon nanoparticle encapsulating an anticancer drug and (ii) a peptide including an amino acid sequence of SEQ ID NO: 1, which binds to the surface of the nanoparticles.

2. The nanoparticles of claim 1, wherein the brain cancer is glioblastoma.

3. The nanoparticles of claim 1, wherein the drug is 7-ethyl-10-hydroxy-camptothecin.

4. The nanoparticles of claim 1, wherein the nanoparticles are taken up by cells through a caveolin receptor.

5. The nanoparticles of claim 1, wherein the nanoparticles pass through the blood-brain barrier (BBB).

6. The nanoparticles of claim 1, wherein the nanoparticles have an average particle size of 100 to 500 nm.

7. The nanoparticles of claim 1, wherein the peptide binds to the surface of the nanoparticles by a poly(ethylene glycol) linker.

8. A method of preparing the nanoparticles of claim 1, the method comprising the following steps:
 (a) preparing porous silicon nanoparticles using a silicon wafer;
 (b) encapsulating an anticancer drug in the nanoparticles; and
 (c) binding a peptide including an amino acid sequence of SEQ ID NO: 1 targeting brain cancer cells to the surface of the nanoparticles encapsulating the anticancer drug by a linker.

9. The method of claim 8, wherein in step (a), the nanoparticles are prepared by preparing a porous silicon film using a silicon wafer, crushing the prepared porous silicon film in an ultrasonic bath, and then filtering the crushed porous silicon film using a syringe filter.

10. The method of claim 8, wherein in step (a), the nanoparticles have an average particle size of 100 to 200 nm.

11. The method of claim 8, wherein in step (b), the drug is 7-ethyl-10-hydroxy-camptothecin.

12. The method of claim 8, wherein the brain cancer is glioblastoma.

13. The method of claim 8, wherein in step (c), the linker is poly(ethylene glycol).

* * * * *